(12) United States Patent
Lupton et al.

(10) Patent No.: US 12,376,818 B2
(45) Date of Patent: Aug. 5, 2025

(54) DOPPLER PROBES, BLOOD FLOW MONITORING SYSTEMS, AND METHODS OF MONITORING BLOOD FLOW

(71) Applicant: CooperSurgical, Inc., Trumbull, CT (US)

(72) Inventors: Jonathan K. Lupton, Thomasville, NC (US); Travis Dillon, Winston-Salem, NC (US)

(73) Assignee: CooperSurgical, Inc., Trumbull, CT (US)

( * ) Notice: Subject to any disclaimer, the term of this patent is extended or adjusted under 35 U.S.C. 154(b) by 241 days.

(21) Appl. No.: 18/210,962

(22) Filed: Jun. 16, 2023

(65) Prior Publication Data
US 2023/0414193 A1    Dec. 28, 2023

Related U.S. Application Data

(60) Provisional application No. 63/354,760, filed on Jun. 23, 2022.

(51) Int. Cl.
*A61B 8/06*    (2006.01)
*A61B 8/00*    (2006.01)

(52) U.S. Cl.
CPC .............. *A61B 8/06* (2013.01); *A61B 8/4227* (2013.01); *A61B 8/4494* (2013.01); *A61B 8/488* (2013.01)

(58) Field of Classification Search
CPC ....... A61B 8/06; A61B 8/4227; A61B 8/4494; A61B 8/488; A61B 8/4209; A61B 8/4483
See application file for complete search history.

(56) References Cited

U.S. PATENT DOCUMENTS

| | | | |
|---|---|---|---|
| 4,926,875 A * | 5/1990 | Rabinovitz | A61B 8/06 600/504 |
| 5,289,821 A | 3/1994 | Swartz | |
| 5,351,693 A | 10/1994 | Taimisto et al. | |
| 6,390,983 B1 | 5/2002 | Mo et al. | |
| 6,939,307 B1 | 9/2005 | Dunlop | |

(Continued)

FOREIGN PATENT DOCUMENTS

WO    2020101680 A1    5/2020

OTHER PUBLICATIONS

United States Patent and Trademark Office, Office Action, U.S. Appl. No. 15/813,574, dated Oct. 18, 2019.

*Primary Examiner* — Peter Luong
(74) *Attorney, Agent, or Firm* — Fish & Richardson P.C.

(57) ABSTRACT

Doppler probes, blood flow monitoring systems, and methods of monitoring blood flow are described. An example probe for monitoring blood flow through a blood vessel includes a retaining member, a first sensor, a first wire member, a second sensor, and a second wire member. The retaining member has a main body that defines an outer surface and an inner surface. The retaining member is moveable between an open configuration and a closed configuration. The inner surface defines a passageway in the closed configuration. The first sensor is disposed on the inner surface of the retaining member. The first wire member is attached to the first sensor and has a first end and a second end. The second sensor is disposed on the first wire member between the first end and the second end of the first wire member. The second wire member is attached to the second sensor.

20 Claims, 9 Drawing Sheets

(56) References Cited

U.S. PATENT DOCUMENTS

| | | |
|---|---|---|
| 7,037,270 B2 | 5/2006 | Seward |
| 7,192,400 B2 | 3/2007 | Campbell et al. |
| 7,421,377 B2 | 9/2008 | Zhang |
| 7,468,039 B2 | 12/2008 | Lui |
| 7,469,598 B2 | 12/2008 | Shkarlet et al. |
| 7,796,247 B2 | 9/2010 | Mao et al. |
| 7,798,968 B2 | 9/2010 | Li |
| 7,822,470 B2 | 10/2010 | Osypka et al. |
| 7,963,920 B2 | 6/2011 | Vilkomerson et al. |
| 8,082,015 B2 | 12/2011 | Yodh et al. |
| 8,728,012 B2 | 5/2014 | Braido |
| 8,798,700 B1 | 8/2014 | Heaton, II et al. |
| 9,028,415 B2 | 5/2015 | Henry |
| 9,345,447 B2 | 5/2016 | Wenzel et al. |
| 9,504,392 B2 | 11/2016 | Caron et al. |
| 9,579,051 B1 | 2/2017 | Mao et al. |
| 10,722,125 B2 | 7/2020 | Tal et al. |
| 11,000,193 B2 | 5/2021 | Tal et al. |
| 11,166,760 B2 | 11/2021 | Arya et al. |
| 2005/0131305 A1 | 6/2005 | Danielson et al. |
| 2006/0149154 A1 | 7/2006 | Stephens et al. |
| 2008/0059098 A1 | 3/2008 | Zhang |
| 2009/0093729 A1 | 4/2009 | Zhang et al. |
| 2012/0245863 A1 | 9/2012 | Rick |
| 2013/0116575 A1 | 5/2013 | Mickle et al. |
| 2015/0208950 A1 | 7/2015 | Akl et al. |
| 2018/0132832 A1 | 5/2018 | Gough |
| 2019/0200907 A1 | 7/2019 | Sarrafzadeh et al. |
| 2019/0209024 A1 | 7/2019 | Zand et al. |
| 2019/0365247 A1 | 12/2019 | Veszelei et al. |
| 2020/0352515 A1 | 11/2020 | Godavarty et al. |
| 2021/0030401 A1 | 2/2021 | King et al. |

\* cited by examiner

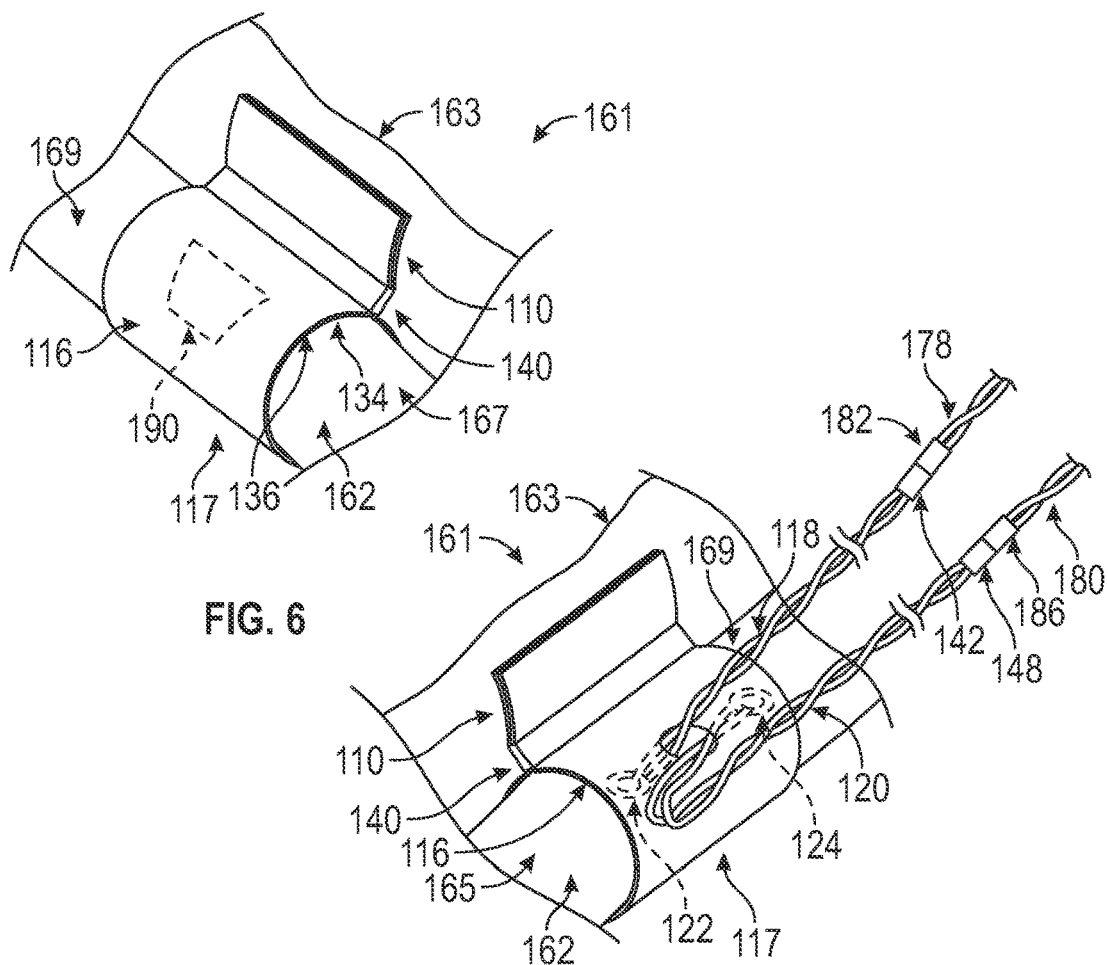
FIG. 6
FIG. 7
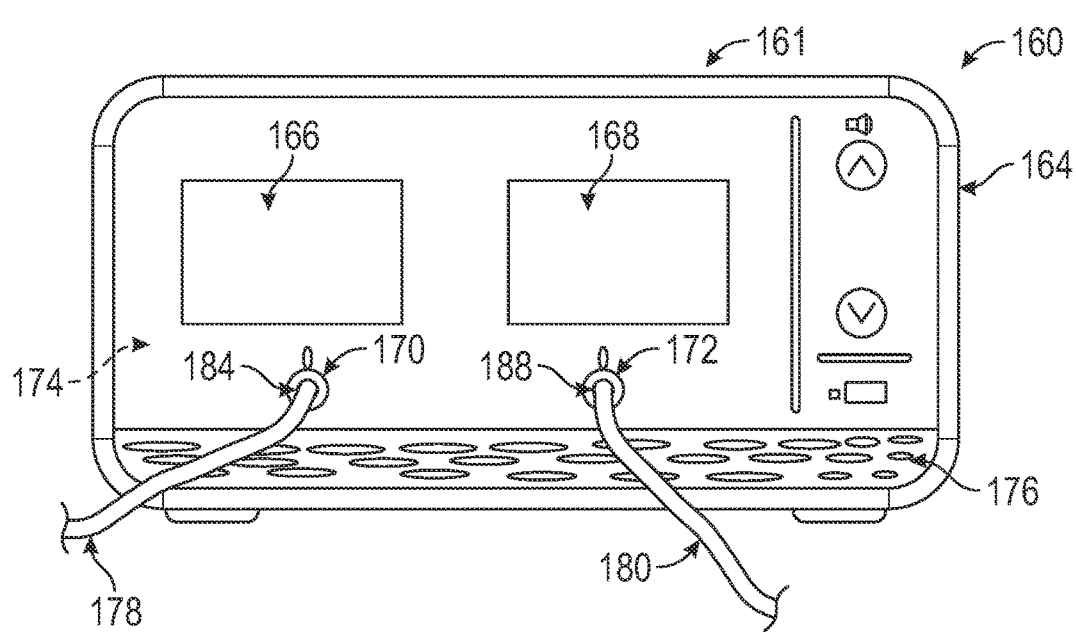
FIG. 8

DOPPLER PROBES, BLOOD FLOW MONITORING SYSTEMS, AND METHODS OF MONITORING BLOOD FLOW

FIELD

The disclosure relates generally to the field of medical devices, medical systems, and associated methods. More particularly, the disclosure relates to Doppler probes, blood flow monitoring systems, and methods of monitoring blood flow.

BACKGROUND

Blood flow monitoring is commonly performed to confirm blood flow through a blood vessel in an implanted tissue flap and the overall health of the flap. Conventionally, a probe that includes a single sensor is attached to a blood flow monitor and positioned such that the sensor contacts the blood vessel of interest. The sensor then provides data to the blood flow monitor, which can be monitored by a clinician. For example, the clinician can monitor audible representations of blood flow through the blood vessel using speakers included in the blood flow monitor and/or visual representations of blood flow using a single visual data point, which is represented as a single bar graph on the monitor (e.g., light emitting diode (LED) bar graph).

Clinicians are trained to qualitatively assess the audible representations provided by blood flow monitors to determine the status of blood flow through blood vessels. In addition, clinicians utilize visual data points as secondary indications of audible representations. However, blood flow monitors that are used in combination with probes that include a single sensor fail to account for weak signals, distorted signals, or excessively noisy anatomical environments, which can result in false positives that lead to unnecessary intervention and false negatives that lead to flap loss. In addition, the inclusion of only a single sensor on a probe fails to provide any redundancy for qualitative indications of blood flow in the event that the sensor loses contact with a blood vessel or otherwise loses the ability to detect blood flow.

This disclosure addresses the need for advanced Doppler probes, blood flow monitoring systems, and methods of monitoring blood flow that can provide improved sound and quantitative data to a clinician relating to blood flow through a vessel.

SUMMARY OF SELECTED EXAMPLE EMBODIMENTS

Various example Doppler probes, blood flow monitoring systems, and methods of using a blood flow monitor are described herein.

An example probe for monitoring blood flow through a blood vessel includes a retaining member, a first sensor, a first wire member, a second sensor, and a second wire member. The retaining member has a main body that defines an outer surface and an inner surface. The retaining member is moveable between an open configuration and a closed configuration. The inner surface defines a passageway in the closed configuration. The first sensor is disposed on the inner surface of the retaining member. The first wire member is attached to the first sensor and has a first end and a second end. The second sensor is disposed on the first wire member between the first end and the second end of the first wire member. The second wire member is attached to the second sensor.

An example blood flow monitoring system for monitoring blood flow through a blood vessel includes a probe and a blood flow monitor. The probe includes a retaining member, a first sensor, a first wire member, a second sensor, and a second wire member. The retaining member has a main body that defines an outer surface and an inner surface. The retaining member is moveable between an open configuration and a closed configuration. The inner surface defines a passageway in the closed configuration. The first sensor is disposed on the inner surface of the retaining member and provides a first signal that contains blood flow data and anatomical noise data. The first wire member is attached to the first sensor and has a first end and a second end. The second sensor is disposed on the first wire member between the first end and the second end of the first wire member. The second sensor provides a second signal that contains anatomical noise data. The second wire member is attached to the second sensor. The blood flow monitor is attached to the first sensor using the first wire member and the second sensor using the second wire member. The blood flow monitor obtains the first signal and the second signal, removes the anatomical noise data obtained from the second signal from the anatomical noise data obtained by the first signal, and creates an adjusted first signal that contains blood flow data from the first signal.

An example method of monitoring blood flow through a blood vessel comprises placing a tissue flap at a point of treatment, the tissue flap having a section of tissue that includes a first blood vessel; attaching a probe to the tissue flap to monitor blood flow through the first blood vessel, the probe attached to the tissue flap such that a first sensor of the probe contacts the first blood vessel and a second sensor of the probe is free of contact with the first blood vessel, the probe including a retaining member, the first sensor, a first wire member, the second sensor, and a second wire member; attaching the first sensor to a blood flow monitor using the first wire member, the blood flow monitor having a first visual display field and a speaker; attaching the second sensor to the blood flow monitor using the second wire member; activating the blood flow monitor, the blood flow monitor obtaining a first signal and a second signal, removing anatomical noise data obtained from the second signal from anatomical noise data obtained by the first signal, and creating an adjusted first signal containing blood flow data from the first signal, the adjusted first signal shown in graphical form on the first visual display field and provided audibly via the speaker; monitoring the adjusted first signal shown in graphical form on the first visual display field over a period of time; determining if the adjusted first signal indicates intervention is required, if intervention is required the method further comprises performing treatment to accomplish intervention, if intervention is not required the method further comprises removing the first sensor from the tissue flap.

Additional understanding of these example Doppler probes, blood flow monitoring systems, and methods of monitoring blood flow can be obtained by review of the detailed description, below, and the appended drawings.

BRIEF DESCRIPTION OF THE DRAWINGS

FIG. 6 is a partial perspective view of the probe illustrated in FIG. 4 attached to a tissue flap.

FIG. 7 is another partial perspective view of the probe illustrated in FIG. 4 attached to a tissue flap.

FIG. 8 is a partial elevation view of the probe illustrated in FIG. 4 attached to an example blood flow monitor. The probe is attached to the monitor using a first extension cable and a second extension cable. The monitor is illustrated in the off state.

DETAILED DESCRIPTION OF SELECTED EXAMPLES

The following detailed description and the appended drawings describe and illustrate various example embodiments of Doppler probes, blood flow monitoring systems, and methods of monitoring blood flow. The description and illustration of these examples are provided to enable one skilled in the art to make and use a Doppler probe, a blood flow monitoring system, and to practice a method of monitoring blood flow. They are not intended to limit the scope of the claims in any manner. The invention is capable of being practiced or carried out in various ways and the examples described and illustrated herein are merely selected examples of the various ways of practicing or carrying out the invention and are not considered exhaustive.

As used herein, "anatomical noise data" relates to data that includes any non-clinically relevant background noise not related to blood flow through a blood vessel of interest (e.g., anatomical noise not related to blood flow) and/or ambient noise not related to blood flow (e.g., noise created by a probe and/or a blood flow monitoring system).

As used herein, "transducer array" refers to a single transducer or an arrangement of a plurality of transducers.

Figure 1:
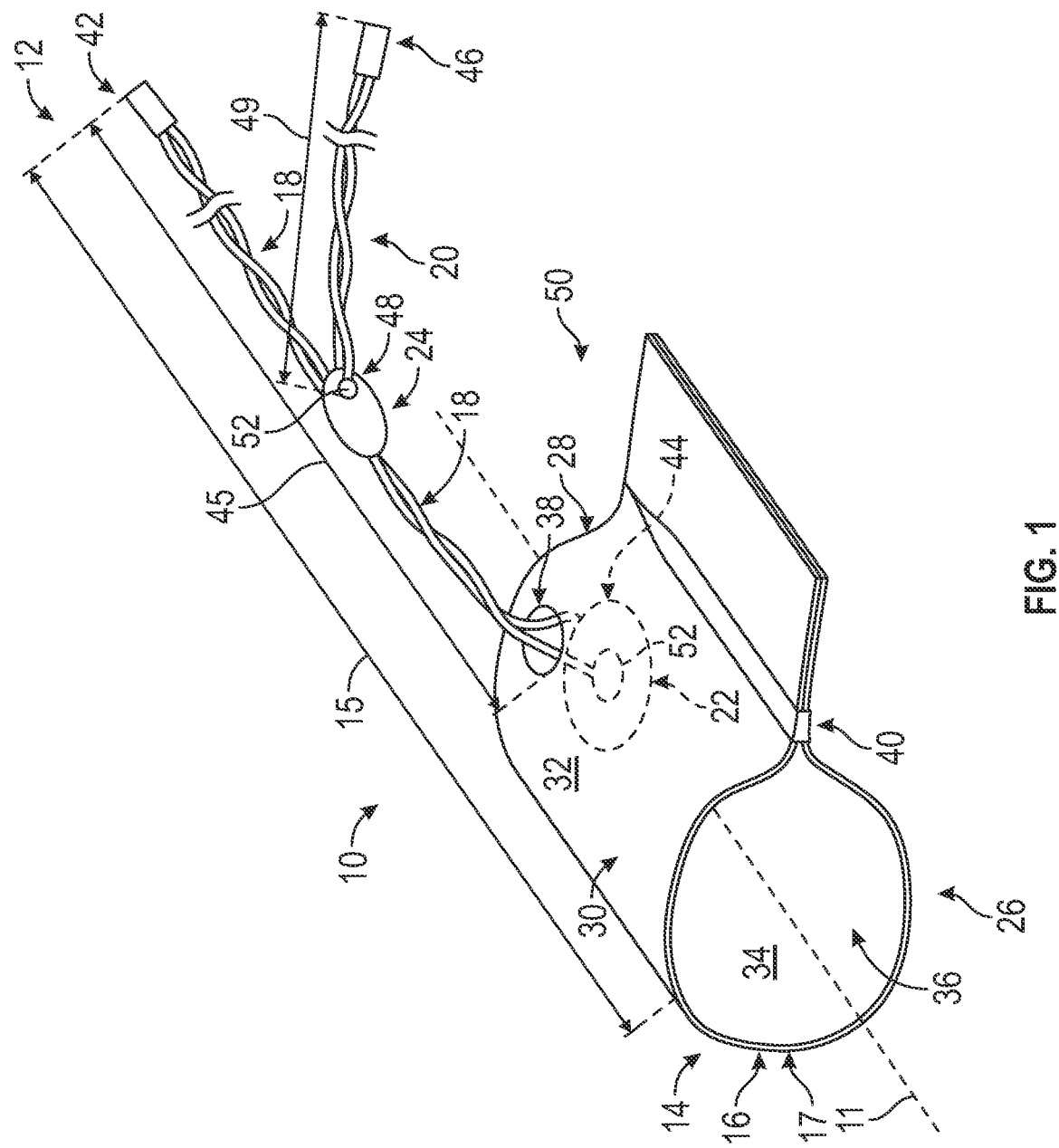
FIG. 1 is a partial perspective view of a first example probe for monitoring blood flow through a blood vessel. The retaining member of the probe is shown in a closed configuration.
Figure 2:
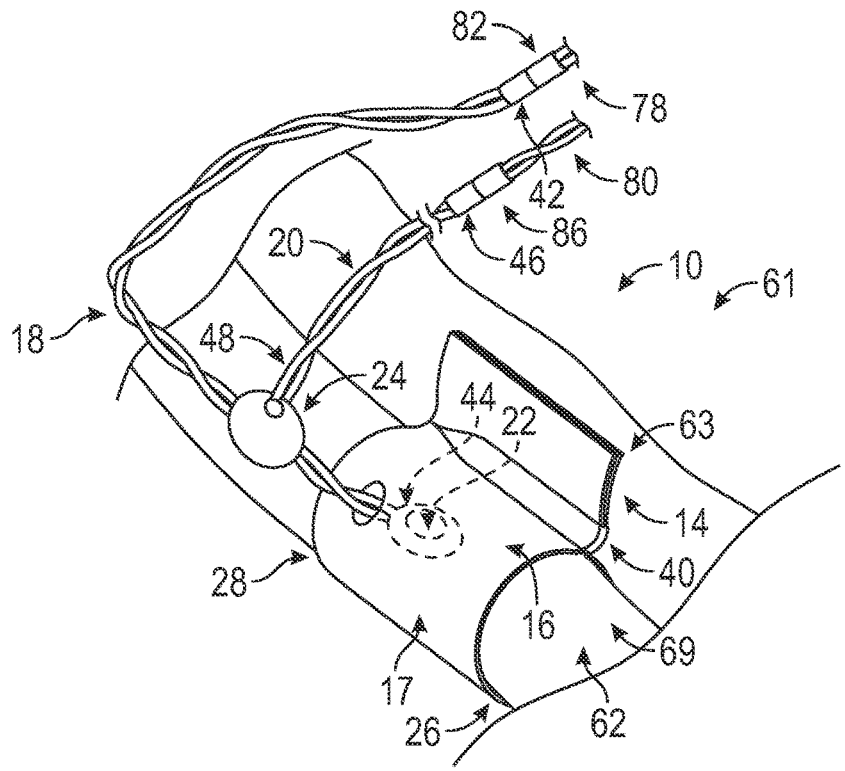
FIG. 2 is a partial perspective view of the probe illustrated in FIG. 1 attached to a tissue flap.

FIGS. 1 and 2 illustrate a first example probe 10 for monitoring blood flow through a blood vessel. The probe 10 has a closed configuration, as shown in FIG. 1, and an open configuration, as described in more detail herein. The probe 10 has a proximal end 12, a distal end 14, a length 15, and includes a retaining member 16, a first wire member 18, a second wire member 20, a first sensor 22, and a second sensor 24. The length 15 of the probe 10 extends from the proximal end 12 to the distal end 14.

In the illustrated embodiment, the retaining member 16 is a cuff 17 disposed at the distal end 14 of the probe 10. The cuff 17 has a lengthwise axis 11 in the closed configuration, a first end 26, a second end 28, and a main body 30 that defines an outer surface 32, and inner surface 34, a passageway 36, and an opening 38. The lengthwise axis 11 extends through the passageway 36. The passageway 36 is defined by the inner surface 34 of the main body 30 when the cuff 17 is in the closed configuration. The opening 38 extends from the outer surface 32 to the inner surface 34 and is sized to receive the first wire member 18. The cuff 17 includes a clip 40 that can be used to position the cuff 17 in the closed position and to attach to the cuff 17 to a blood vessel. However, alternative embodiments can omit the inclusion of a clip and utilize other structure (e.g., sutures) to maintain a retaining member, such as a cuff, in a closed configuration during use.

While the retaining member 16 has been illustrated as a cuff 17, a probe can include any suitable retaining member having any suitable structural arrangement to which one or more sensors can be attached and that is capable of accomplishing attachment between the retaining member and a blood vessel. Examples of retaining members considered suitable for inclusion in a probe include cuffs, clips, sutures, adhesive pads, bands, and any other retaining member considered suitable for a particular embodiment.

The first wire member 18 has a first end 42, a second end 44, and a length 45 that extends from the first end 42 to the second end 44. The first end 42 of the first wire member 18 is configured to be attached to a blood flow monitor (e.g., via an extension cable) such that signals and/or data can be communicated from the first sensor 22 to the blood flow monitor, and vice versa, during use. The second end 44 of the first wire member 18 is attached to the first sensor 22. The second wire member 20 has a first end 46, a second end 48, and a length 49 that extends from the first end 46 to the second end 48. The first end 46 of the second wire member 20 is configured to be attached to a blood flow monitor (e.g., via an extension cable) such that signals and/or data can be communicated from the second sensor 24 to the blood flow monitor, and vice versa, during use. The second end 48 of the second wire member 20 is attached to the second sensor 24. A wire member included in a probe can include any suitable wire, bundle of wires, cable, or other structure capable of transmitting signals and/or data from a sensor to a blood flow monitor and/or from a blood flow monitor to a sensor.

The first sensor 22 is attached to the distal end 14 of the probe 10, is attached to the second end 44 of the first wire member 18, and monitors blood flow through a blood vessel during use. The first sensor 22 is positioned such that the first sensor 22 directly contacts a blood vessel when the probe 10 is disposed on a blood vessel. In the illustrated embodiment, the first sensor 22 is releasably attached to, and disposed on, the inner surface 34 of the retaining member 16 (e.g., cuff 17). However, in alternative embodiments, a first sensor can be fixedly attached to a retaining member, such as a cuff, such that removal of the first sensor from the retaining member would result in damage to the retaining member and/or the first sensor. During use, the first sensor 22 provides a first signal that contains blood flow data and anatomical noise data to a blood flow monitor to which the first sensor 22 is attached via the first wire member 18. The blood flow data relates to the blood flow through the blood vessel to which to probe 10 is attached and the first sensor 22 contacts. The anatomical noise data relates to anatomical noise (e.g., non-clinically relevant background noise not related to blood flow) received by the first sensor 22 during use.

The second sensor 24 is disposed proximal to the first sensor 22. In the illustrated embodiment, the second sensor 24 is disposed on the first wire member 18 between the proximal end 12 of the probe 10 and the distal end 14 of the probe 12. More specifically, the second sensor 24 is disposed on the first wire member 18 between the first end 42 of the first wire member 18 and the second end 44 of the first wire member 18. As shown in FIG. 2, the second sensor 24 is disposed on the first wire member 18 between the first end 42 of the first wire member 18 and the retaining member (e.g., cuff 17). In the embodiment shown, the second sensor 24 is releasably attached to the first wire member 18 and is free of attachment to the retaining member (e.g., cuff 17). However, in alternative embodiments, a second sensor can be fixedly attached to a first wire member such that removal of the second sensor from the first wire member would result in damage to the first wire member and/or the second sensor. Alternative to, or in combination with, attaching a second sensor to a first wire member, a second wire member can be attached to a first wire member (e.g., releasably (e.g., using adhesive), or fixedly). The second sensor 24 is attached to the second end 48 of the second wire member 20 and monitors anatomical noise. During use, the second sensor 24 is positioned such that it is free of contact with the blood vessel to which the probe 10 (e.g., cuff 17) is attached and is free of contact with the blood vessel the first sensor 22 directly contacts. During use, the second sensor 24 provides a second signal that contains anatomical noise data that relates to anatomical noise (e.g., non-clinically relevant background noise not related to blood flow) received by the second sensor 24 during use. In the embodiment shown, the probe 10 is a Doppler probe 50 and each of the first sensor 22 and the second sensor 24 is a probe crystal 52 (e.g., crystal assembly, crystal transducer).

The second sensor 24 can be positioned on a first wire member 18 at any suitable location that positions the second sensor 24 such that it is free of contact from a blood vessel intended to be contacted by the first sensor 22 and such that the second sensor 24 is disposed within an anatomy of a patient within which the probe 10 is intended to be disposed. Examples of locations considered suitable to position a second sensor relative to a first sensor and/or relative to a blood vessel include locations in which a second sensor is disposed a distance from a first sensor that is equal to, greater than, less than, or about 5 millimeters, 10 millimeters, 15 millimeters, 20 millimeters, 25 millimeters, 30 millimeters, 15 centimeters, locations in which a second sensor is disposed a distance from a first sensor that is between about 5 millimeters and about 15 millimeters, locations in which a second sensor is disposed a distance from a first sensor that is less than or equal to about 15 centimeters, locations in which a second sensor is disposed proximal to a first sensor, locations in which a second sensor is disposed within an anatomy of a patient during use, locations in which a second sensor is disposed a distance from a distal end of a probe that is equal to, greater than, less than, or about 5 millimeters, 10 millimeters, 15 millimeters, 20 millimeters, 25 millimeters, 30 millimeters, locations in which a second sensor is disposed a distance from a distal end of a probe that is between about 5 millimeters and about 15 millimeters, locations in which a second sensor is disposed a distance from a distal end of a probe that is less than or equal to about 15 centimeters, locations in which a second sensor is disposed a distance from a first sensor or a distal end of a probe that is equal to, greater than, less than, or about 10% of a probe length (e.g., about 140 centimeters without an extension cable, about 193 centimeters with an extension cable), about 20% of a probe length, about 30% of a probe length, about 40% of a probe length, about 50% of a probe length, locations in which a second sensor is disposed a distance from a first sensor or a distal end of a probe that is between about 10% and about 50% of a probe length, and any other location considered suitable for a particular embodiment.

Figure 2B:
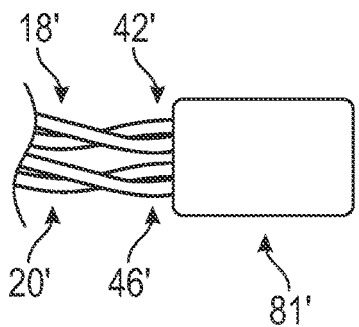
FIG. 2B is a partial top view of an alternative first wire member, second wire member, and connector of a probe.

Alternative embodiments can include a second sensor that is positioned at locations other than on a first wire member. For example, a second sensor can be attached to an inside surface of a retaining member, such as a cuff, attached to an outside surface of a retaining member, such as a cuff, attached to a first sensor, or be free floating within a patient anatomy and located a distance from a first sensor and/or distal end as described herein. A second sensor, for example, can be positioned on a retaining member, such as a cuff, a first sensor, a blood vessel, a first wire member, and/or a second wire member such that a sensing portion (e.g., probe crystal) of the second sensor is facing substantially opposite (e.g., is disposed 180 degrees, is disposed between about 90 degrees and about 270 degrees) relative to a sensing portion (e.g., probe crystal) of a first sensor. FIG. 2C illustrates a first sensor 22" attached to a blood vessel 62" using a retaining member 16", which is a suture 17", and a second sensor 24" attached to the first sensor 22" (e.g., using adhesive). The sensing portion 53" (e.g., probe crystal 52") of the second sensor 24" is facing substantially opposite (e.g., is disposed 180 degrees) relative to the sensing portion 53" (e.g., probe crystal 52") of the first sensor 22".

While the probe 10 has been illustrated as a Doppler probe 50 and each of the first and second sensors 22, 24 has been illustrated as a probe crystal 52, a probe can comprise any suitable type of probe and can include any suitable type of sensor and selection of a suitable probe and/or sensor can be based on various considerations, such as the type and/or location of a blood vessel being monitored. Examples of probes considered suitable to include the features, structure, and/or components described herein include in vivo probes, ultrasonic probes, electromagnet probes, Doppler probes, such as the Cook-Swartz Doppler probe, and any other probes considered suitable for a particular embodiment. Examples of sensors considered suitable to include in a probe include transducers, transducer arrays, piezo crystals, piezoelectric crystals, sensors that include components capable of transmitting and/or receiving signals and/or data, sensors that include components capable of transmitting and/or receiving signals and/or data wirelessly, sensors that emit and/or receive any suitable signal having any suitable frequency, sensors that have any suitable footprint, combinations of the sensors described herein, and any other sensor considered suitable for a particular embodiment. While the probe 10 has been illustrated as including various components, a probe can include any suitable number of components. Selection of a suitable number of components for a probe to include can be based on various considerations, including the material forming the probe, or portions of the probe, and/or the size and/or location of a blood vessel to which the probe is intended to be attached.

Figure 3:
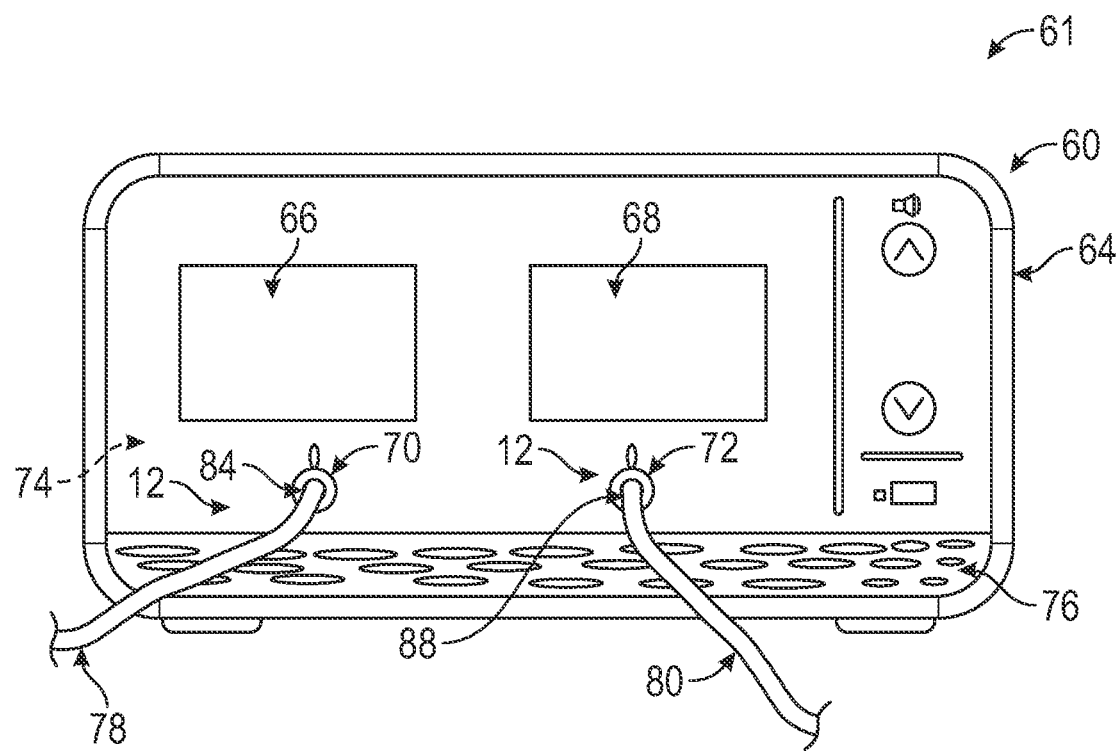
FIG. 3 is a partial elevation view of the probe illustrated in FIG. 1 attached to an example blood flow monitor. The probe is attached to the monitor using a first extension cable and a second extension cable. The monitor is illustrated in the off state.

FIGS. 2 and 3 illustrate an example blood flow monitoring system 61 that includes the probe 10 attached to a blood flow monitor 60. FIGS. 2 and 3 illustrate the probe 10 attached to the blood flow monitor 60 and a blood vessel 62. The blood flow monitor 60 has a housing 64, a first visual display field 66, a second visual display field 68, a first channel port 70, a second channel port 72, a processor 74, and a speaker 76. The blood flow monitor 60 is moveable between an off state and an on state. FIG. 3 illustrates the blood flow monitor 60 in the off state. The processor 74 is disposed within the housing 64 and is connected to each of the first visual display field 66, second visual display field 68, the first channel 70, the second channel port 72, and the speaker 76. Is use, the speaker 76 emits sounds, such as those that relate to signals and/or data provided by the first signal and/or second signal, which allow a clinician to listen to sounds relating to blood flow through a blood vessel and/or anatomical noise. Optionally, the blood flow monitor 60 can automatically detect the probe 10 (e.g., the first sensor 22 and/or second sensor 24) when connected to the blood flow monitor 60 via the first and second channel ports 70, 72.

In the illustrated embodiment, the first sensor 22 is attached to the blood flow monitor 60 using a first extension cable 78 and the second sensor 24 is attached to the blood flow monitor 60 using a second extension cable 80. The first extension cable 78 has a first end 82 attached to the first wire member 18 (e.g., first end 42 of the first wire member 18) and a second end 84 attached to the blood flow monitor 60 (e.g., first channel port 70). The second extension cable 80 has a first end 86 attached to the second wire member 20 (e.g., first end 46 of the second wire member 20) and a second end 88 attached to the blood flow monitor 60 (e.g., second channel port 72). However, in alternative embodiments, a first sensor and/or a second sensor can be attached directly to a blood flow monitor without using an extension cable. For example, a blood flow monitor can be attached to a first sensor using a first wire member and a second sensor using a second wire member. Alternatively, as shown in FIG. 2B, a first end 42' of a first wire member 18' and a first end 46' of a second wire member 20' can be disposed within a single connector 81' that can be attached to a monitor or an extension cable for simplified removal from a patient anatomy.

When the blood flow monitor 60 is in the on state, the first visual display field 66 shows an adjusted first signal in graphical form and the second visual display field 68 shows the second signal received from the second sensor 24 in graphical form. In use, the blood flow monitor 60 obtains the first signal and the second signal, removes the anatomical noise data obtained from the second signal from the anatomical noise data obtained by the first signal, and creates an adjusted first signal that contains blood flow data from the first signal. For example, the processor 74 of the blood flow monitor 60 uses signals and/or data received via the first and second channel ports 70, 72 in combination with one another to remove the anatomic noise data of the second signal (e.g., received from the second sensor 24) from the anatomical noise data of the first signal (e.g., received from the first sensor 22) such that the adjusted first signal is created and contains only the blood flow data of the first signal, or only the blood flow data and a portion of the anatomical noise data of the first signal. This adjusted first signal can be provided to a clinician via the first visual display field 66 and/or audibly via the speaker 76. Creating an adjusted first signal is considered advantageous at least because a first visual display field 66 can show only data relating to the adjusted first signal in graphical form (e.g., blood flow data in graphical form and omitting all, or a portion of, the anatomical noise data of the first signal) and/or the speaker 76 can emit sounds relating to only the adjusted first signal (e.g., blood flow through a vessel and omitting all, or a portion of, the anatomical noise), which increases the reliability of the data relating to the blood vessel being presented to a clinician. In addition to providing the adjusted first signal, in use the processor 74 can also provide the second signal in to a clinician via the second visual display field 68 (e.g., in graphical form) and/or the speaker 76. For example, the second visual display field 68 can show anatomical noise data received from the second sensor 24 in graphical form that relates to anatomical noise from within the anatomy of the patient. Optionally, the blood flow monitor can be manipulated such that a first visual display field and/or a second visual display field can present a first signal in graphical form, an adjusted first signal in graphical form, and/or a second signal in graphical form and/or such that one or more visual display fields can be combined (e.g., when reviewing a channel's historical blood flow data). Optionally, a processor, or separate amplifier, can be used to amplify a first signal, an adjusted first signal, and/or a second signal such that blood flow data can be amplified to improve signal strength and/or audibility.

The graphical form of the first signal and/or adjusted first signal shown in the first visual display field 66 can be presented to a clinician in any suitable format, such as presenting blood flow over time, a sound graphic, and/or a visual representation of blood flow velocity in graphical form. The graphical form of the second signal shown in the second visual display field 68 can be presented to a clinician in any suitable format, such as presented anatomic noise over time, a sound graphic, and/or a visual representation of anatomic noise in graphical form. The data provided in the first visual display field 66 and/or the second visual display field 68 in graphical form can be shown in real-time, be held or frozen, or a clinician can select a window of time (e.g., adjustable, clinician-defined) within which the clinician would like to review data. Inclusion of the first and second visual display fields 66, 68 is considered advantageous at least because they allow a clinician to review, or monitor, trend data relating to blood flow over time. For example, the first and second visual display fields 66, 68 allow a clinician to review, or monitor, trend data relating to blood flow (e.g., over time) and anatomic noise (e.g., over time).

While the blood flow monitor 60 has been illustrated as having a particular number of visual display fields (e.g., discrete portions of a display, discrete displays) and as having a particular number of channel ports, a blood flow monitor can include any suitable number of visual display fields, channel ports, and other components, features, and/or devices. Selection of a suitable number of visual display fields and/or channel ports to include in a blood flow monitor can be based on various considerations, including the number of sensors being utilized to monitor a blood vessel and/or anatomic noise. Examples of numbers of visual display fields and/or channel ports considered suitable to include in a blood flow monitor include one, at least one, two, a plurality, three, four, five, more than five, and any other number considered suitable for a particular embodiment. Examples of other components, features, and/or devices considered suitable to include in a blood flow monitor include those described herein, one or more speakers, one or more amplifiers, and any other component considered suitable for a particular embodiment. Depending on the type of sensors being utilized, a blood flow monitor can also include one or more components capable of receiving and/or transmitting signals and/or data wirelessly, such as receiving signals and/or data wirelessly from one or more sensors and/or transmitting signals and/or data wirelessly to a network such that signals and/or data received by one or more sensors and/or signals and/or data displayed within a visual display field can be provided to a remote device (e.g., remote storage device) and/or a clinician via a remote app and/or web browser (e.g., on a mobile device, on a tablet, on a cellular phone).

Furthermore, a blood flow monitor to which a probe is attached can be any suitable blood flow monitor, such as a Doppler blood flow monitor. Selection of a suitable blood flow monitor to attach a probe can be based on various considerations, such as the type of blood vessel being monitored and/or the procedure that has been, or is intended to be, completed. Examples of blood flow monitors considered suitable to attach a probe, a first sensor, and/or a second sensor include Doppler blood flow monitors, blood flow monitors that include a speaker, blood flow monitors capable of emitting sounds (e.g., Doppler sounds) relating to blood flow through a blood vessel (e.g., via speaker), blood flow monitors that can monitor blood flow through a blood vessel, combinations of those described herein, and any other blood flow monitor considered suitable for a particular embodiment. A blood flow monitor can include any software and/or components capable of receiving and/or transmitting signals and/or data (e.g., over a network, such as the internet).

As shown in FIG. 2, the probe 10 is attached to the blood vessel 62 of a tissue flap 63 such that the first sensor 22 contacts the blood vessel 62 and the second sensor 24 is disposed within the body (e.g., anatomy) of the patient and does not directly contact the blood vessel 62. This can be accomplished by positioning the cuff 17 in the open configuration on the blood vessel 62 such that the inner surface 34 and the first sensor 22 contact the blood vessel 62 and subsequently moving the cuff 17 to the closed position and positioning the clip 40 on the cuff 17. This results in the cuff 17 being attached to the blood vessel 62 and the blood vessel 62 being disposed within passageway 36. The second sensor 24 is positioned within the anatomy of the patient such that the second sensor 24 does not directly contact the blood vessel 62 and is not external to the patient. In the illustrated embodiment, the cuff 17 is attached to a vein 69 such that the first sensor 22 contacts the vein 69 and the second sensor 24 is disposed within the anatomy of the patient (e.g., on the first wire member 18). However, in alternative embodiments, a retaining member, such as a cuff, can be positioned at any suitable location on, or within, a tissue flap and can be attached to any suitable blood vessel, such as an artery, such that a first sensor contacts a portion of the tissue flap (e.g., artery).

While the probe 10 has been illustrated as being attached to a blood vessel 62 of a tissue flap 63, a probe can be positioned on any suitable blood vessel of any suitable section of tissue, such as tissues that can be used to complete an autologous tissue reconstruction procedure, tissues that include at least one blood vessel, and/or tissues that have been moved from a donor site of a patient to a recipient site of the patient. Examples of sections of tissue considered suitable to position a probe include local flaps (e.g., advancement flaps, rotation flaps, transposition flaps, interpolation flaps), free flaps, transverse rectus abdominis muscle flaps, deep inferior epigastric perforator flaps, latissimus dorsi flaps, gluteal artery perforator flaps, transverse upper gracilis flaps, flaps obtained from the chest, breast, back, abdomen, arms, buttocks, or legs (e.g., thighs) of a patient, combinations of those described herein, and any other tissue flap or section considered suitable for a particular embodiment.

Figure 2A:
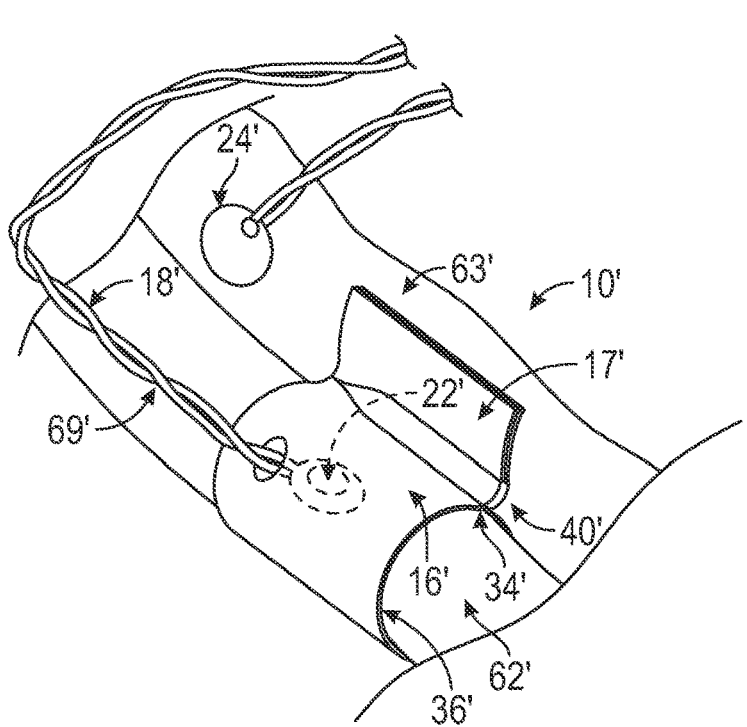
FIG. 2A is a partial perspective view of an alternative probe attached to a tissue flap.
Figure 2C:
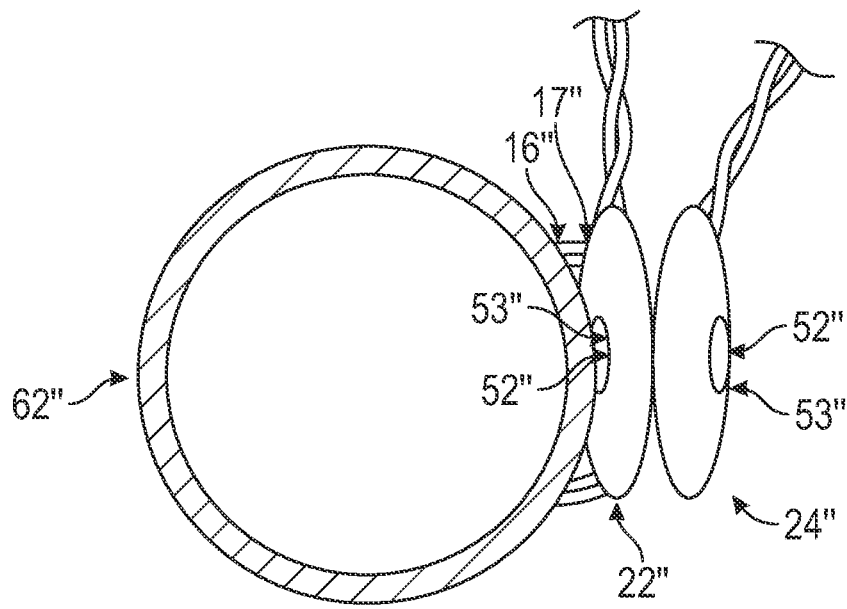
FIG. 2C is a partial sectional view of a blood vessel and an alternative probe attached to the blood vessel.

Alternatively, as shown in FIG. 2A, a second sensor 24' can be free of a first wire member 18' and attached directly to the tissue flap 63'. As shown in FIG. 2A, the probe 10' is attached to the blood vessel 62' of a tissue flap 63' such that the first sensor 22' contacts the blood vessel 62' and the second sensor 24' is disposed within the body (e.g., anatomy) of the patient and does not directly contact the blood vessel 62'. This can be accomplished by positioning the cuff 17' in the open configuration on the blood vessel 62' such that the inner surface 34' and the first sensor 22' contact the blood vessel 62' and subsequently moving the cuff 17' to the closed position and positioning the clip 40' on the cuff 17'. This results in the cuff 17' being attached to the blood vessel 62' and the blood vessel 62' being disposed within passageway 36'. The second sensor 24' is positioned within the anatomy of the patient such that the second sensor 24' does not directly contact the blood vessel 62' and is not external to the patient. In the illustrated embodiment, the cuff 17' is attached to a vein 69' such that the first sensor 22' contacts the vein 69' and the second sensor 24' is disposed within the anatomy of the patient (e.g., on the tissue flap 63'). However, in alternative embodiments, a second sensor can be free of attachment to a tissue flap and can be positioned at any suitable location within the anatomy of a patient. A second sensor can be attached to a tissue flap, or be disposed within the anatomy of a patient, such that the second sensor is free of contact from a blood vessel intended to be contacted by a first sensor and such that the second sensor is disposed within the anatomy of a patient within which a probe is intended to be disposed. Examples of locations considered suitable to position a second sensor relative to a first sensor and/or relative to a blood vessel are described herein.

Probes that include a first sensor that monitors blood flow through a blood vessel and creates a first signal and that include a second sensor that monitors anatomical noise and creates a second signal, which can be used to modify the first signal resulting in an adjusted first signal, are considered advantageous at least because the adjusted first signal allows clinicians to more clearly visualize, hear, and/or understand blood flow through a vessel being monitored. This allows for a reduction in false positives that lead to unnecessary intervention and false negatives that lead to flap loss. For example, use of probes that include first and second sensors, such as probe 10, can be used to remove, or filter, non-clinically beneficial noise (e.g., anatomical noise, ambient environmental noise, system noise) from a signal that includes blood flow data, which produces a clearer indication of blood flow to the clinician via the blood flow monitor to which the probe is attached. Furthermore, these probes can be attached to both channel ports of a blood flow monitor to provide qualitative assessment of blood flow velocity, including audible and visual blood flow indications. Conventional probes that include only a single sensor provide signals that include both blood flow data and anatomical noise data, which require clinicians to determine what portion of the detected signal is clinically relevant. This can be difficult depending on the strength of the received signal.

Figure 4:
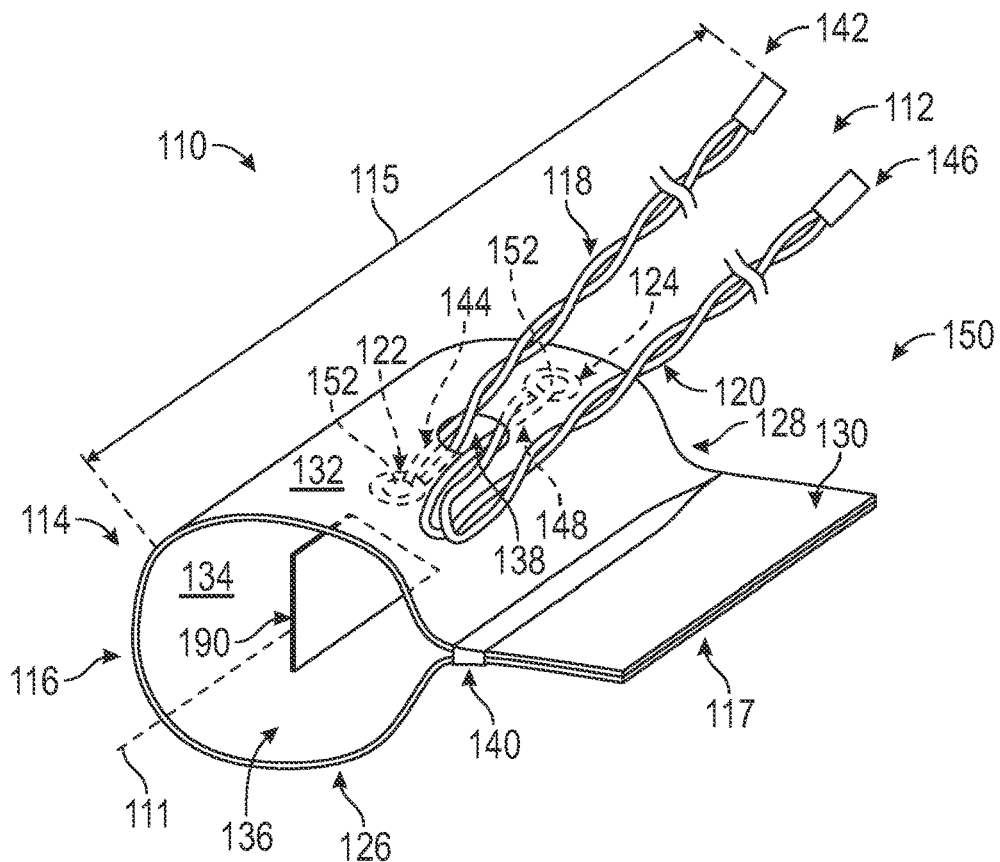
FIG. 4 is a partial perspective view of a second example probe for monitoring blood flow through a blood vessel. The retaining member of the probe is shown in a closed configuration.
Figure 5:
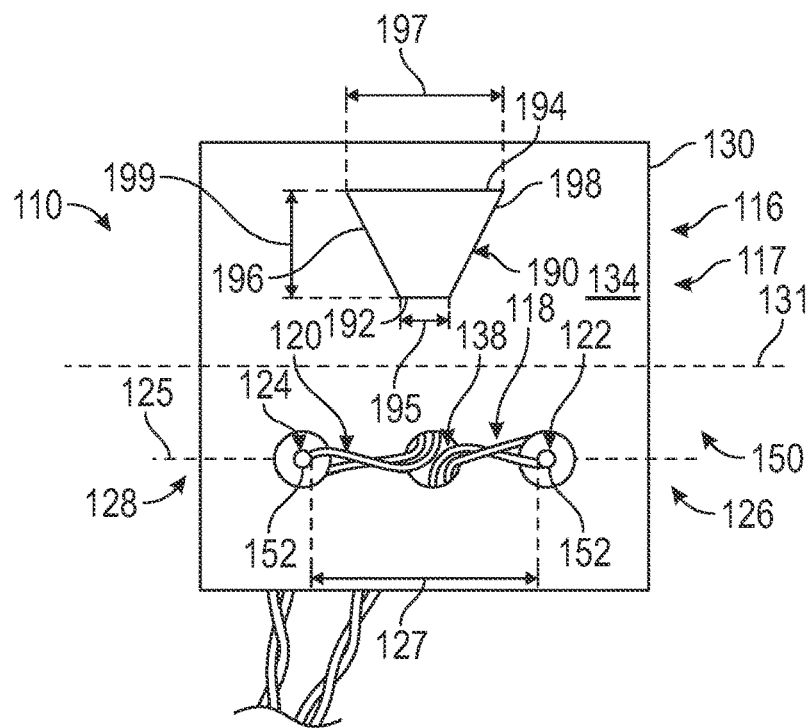
FIG. 5 is a partial top view of the probe illustrated in FIG. 4. The retaining member of the probe is shown in an open configuration.

FIGS. 4, 5, 6, and 7 illustrate a second example probe 110 for monitoring blood flow through a blood vessel. The probe 110 has a closed configuration, as shown in FIGS. 4, 6, and 7, and an open configuration, as shown in FIG. 5. The probe 110 a proximal end 112, a distal end 114, a length 115, and includes a retaining member 116, a first wire member 118, a second wire member 120, a first sensor 122, a second sensor 124, and a reflector 190. The length 115 of the probe 110 extends from the proximal end 112 to the distal end 114.

In the illustrated embodiment, the retaining member 116 is a cuff 117 that is disposed at the distal end 114 of the probe 110. The cuff 117 has a lengthwise axis 111 when in the closed configuration, a first end 126, a second end 128, and a main body 130 that has a lengthwise axis 131 and defines an outer surface 132, an inner surface 134, a passageway 136, and an opening 138. The lengthwise axis 111 of the cuff 117 extends through the passageway 136. The lengthwise axis 131 of the main body 130 extends from the first end 126 to the second end 128 along the inner surface 134. The passageway 136 is defined by the main body 130 when the cuff 117 is in the closed configuration. The opening 138 extends from the outer surface 132 to the inner surface 134 and is sized to receive the first wire member 118 and the second wire member 120. The cuff 117 includes a clip 140 that can be used to position the cuff 117 in the closed position and to attach to the cuff 117 to a blood vessel, as shown in FIGS. 6, and 7.

The first wire member 118 has a first end 142 and a second end 144. The first end 142 of the first wire member 118 is configured to be attached to a blood flow monitor (e.g., via an extension cable) such that signals and/or data can be communicated from the first sensor 122 to the blood flow monitor, and vice versa, during use. The second end 144 of the first wire member 118 is attached to the first sensor 122. The second wire member 120 has a first end 146 and a second end 148. The first end 146 of the second wire member 120 is configured to be attached to a blood flow monitor (e.g., via an extension cable) such that signals and/or data can be communicated from the second sensor 124 to the blood flow monitor, and vice versa, during use. The second end 148 of the second wire member 120 is attached to the second sensor 124.

The first sensor 122 is attached to the distal end 114 of the probe 110. The first sensor 122 is releasably attached to the inner surface 134 of the cuff 117 and is positioned such that the first sensor 122 directly contacts a blood vessel when the probe 110 is disposed on a blood vessel. The first sensor 122 is attached to the second end 144 of the first wire member 118 and monitors blood flow through a blood vessel. During use, the first sensor 122 provides a first signal that contains blood flow data to a blood flow monitor to which the first sensor 122 is attached via the first wire member 118. The blood flow data in the first signal relates to the blood flow through a blood vessel to which to probe 110 is attached and the first sensor 122 contacts.

The second sensor 124 is attached to the distal end 114 of the probe 110. The second sensor 124 is releasably attached to the inner surface 134 of the cuff 117 and is positioned such that the second sensor 124 directly contacts a blood vessel when the probe 110 is disposed on a blood vessel. The second sensor 124 is attached to the second end 148 of the second wire member 120 and monitors blood flow through a blood vessel. During use, the second sensor 124 provides a second signal that contains blood flow data to a blood flow monitor to which the second sensor 124 is attached via the second wire member 120. The blood flow data in the second signal relates to the blood flow through a blood vessel to which to probe 110 is attached and the second sensor 124 contacts. In the embodiment shown, the probe 110 is a Doppler probe 150 and each of the first sensor 122 and the second sensor 124 is a probe crystal 152 (e.g., crystal assembly, crystal transducer). Optionally, a second sensor can be attached to a separate, second retaining member, such as a cuff, and attached to a blood vessel.

The first sensor 122 and the second sensor 124 are separated from one another by a distance 127. The first sensor 122 and the second sensor 124 are aligned on the cuff 117 such that they are disposed on an axis 125 that is substantially parallel to the lengthwise axis 111 of the cuff 117 and the lengthwise axis 131 of the main body 130. However, alternative embodiments can include a first sensor that is disposed on a first axis and a second sensor that is disposed on a second axis. Each of the first and second axes can be different from one another (e.g., non-coaxial) and be disposed substantially parallel to a lengthwise axis of a retaining member, such as a cuff, and a lengthwise axis of a main body of the retaining member. Examples of distances considered suitable to separate a first sensor and a second sensor include distances equal to, greater than, less than, and about 3 millimeters, 4 millimeters, 5 millimeters, 6 millimeters, 7 millimeters, 8 millimeters, 9 millimeters, 10 millimeters, distances between about 3 millimeters and about 10 millimeters, and any other distance considered suitable for a particular embodiment.

The reflector 190 is formed of a reflective material, is attached to the inner surface 134 of the cuff 117, and is directed toward the first and second sensors 122, 124 when the cuff 117 is in the closed position (e.g., the cuff 117 is positioned on a blood vessel). In the illustrated embodiment, the reflector 190 is disposed substantially opposite the first and second sensors 122, 124 relative to the lengthwise axis 111 when the cuff 117 is in the closed position, as shown in FIGS. 4, 6, and 7. This structural arrangement results in a hypothetical plane that contains the lengthwise axis 111 and extends through each of the first and second sensors 122, 124 and the reflector 190. However, alternative embodiments can omit a reflector and/or include a reflector that is offset relative to a first sensor and/or a second sensor, such that a first hypothetical plane that contains a lengthwise axis of a retaining member, such as a cuff, extends through a first sensor and/or a second sensor and a second hypothetical plane that contains a lengthwise axis of the retaining member extends through a reflector. The first hypothetical plane can be disposed at any suitable angle relative to the second hypothetical plane, such as angles equal to, less than, greater than, or about 90 degrees, 180 degrees, between about 1 degree and about 90 degrees, between about 1 degree and about 180 degrees, and any other angle considered suitable for a particular embodiment.

In the illustrated embodiment, the reflector 190 has a variable width. As shown in FIG. 5, the reflector 190 has a first side 192, a second side 194, a third side 196, and a fourth side 198, a first width 195, a second width 197, and a first height 199. In the illustrated embodiment, the first and second sides 192, 194 are parallel to the lengthwise axis 131 of the main body 130. The first side 192 has the first width 195 and the second side 194 has the second width 197. The second width 197 is greater than the first width 195 and the first height 199. The third side 196 extends from the first side 192 to the second side 194. The fourth side 198 extends from the first side 192 to the second side 194. As shown in FIG. 5, the width of the reflector 190 varies. More specifically, the width of the reflector 190 tapers from the second side 194 to the first side 192.

While the reflector 190 has been illustrated as being positioned on the inner surface 134, as being oriented in a particular manner, and as having a particular structural arrangement, a reflector can be positioned on any suitable portion of a retaining member, such as a cuff, in any suitable orientation (e.g., relative to a lengthwise axis of a retaining member), and/or have any suitable structural arrangement that includes a variable width. For example, a reflector can be positioned on an inner surface of a retaining member, an outer surface of a retaining member, an end of a retaining member, within the material forming a retaining member, deposited on a retaining member, be a portion of a retaining member that is formed of a first material that is different than a second material that forms a remaining portion of the retaining member, and/or be a portion of the retaining member that has a first thickness that is different than a second thickness of the material that forms a remaining portion of the retaining member. Examples of suitable numbers of sides for a reflector include one, at least one, two, a plurality, three, four, five, more than five, and any other number considered suitable for a particular embodiment. A side of a reflector can be straight, curved, or have any other suitable structure considered suitable for a particular embodiment. Examples of variable widths considered suitable to include on a reflector include those in which a width tapers from a first side to a second side, a width that tapers from a second side to a first side, a width that tapers from a third side to a fourth side, a width that tapers from a fourth side to a third side, and any other variable width considered suitable for a particular embodiment. A width can be positioned on any suitable portion of a reflector (e.g., side) and is not required to be positioned on a side of a reflector that is disposed parallel to a lengthwise axis of a retaining member.

A reflector can be formed of any suitable ultrasonic reflective material and selection of a suitable material to form a reflector can be based on various considerations, such as the type of sensor(s) included in a probe. Examples of materials considered suitable to form a reflector include silicon, plastics, biocompatible materials, biocompatible material surface or injection treatments, any material with a quantifiable increase in acoustic impedance from blood and/or soft tissue which is between about 1.6 MRayl and about 1.69 MRayl, and any other material considered suitable for a particular embodiment. Alternative embodiments can replace a reflector with an absorber (e.g., structure that absorbs reflected waves). Examples of materials considered suitable to form an absorber include silicon rubber, polyurethane rubber, foam (e.g., air-loaded) materials, and any other material considered suitable for a particular embodiment.

FIGS. 6, 7, and 8 illustrate another example blood flow monitoring system 161 that includes the probe 110 attached to a blood flow monitor 160. FIGS. 6, 7, and 8 illustrate the probe 110 attached to the blood flow monitor 160 and a blood vessel 162. The blood flow monitor 160 has a housing 164, a first visual display field 166, a second visual display field 168, a first channel port 170, a second channel port 172, a processor 174, and a speaker 176. The blood flow monitor 160 is moveable between an off state and an on state. FIG. 8 illustrates the blood flow monitor 160 in the off state. The processor 174 is disposed within the housing 164 and is connected to each of the first visual display field 166, second visual display field 168, the first channel 170, the second channel port 172, and the speaker 176. In use, the speaker 176 emits sounds, such as those that relate to signals and/or data provided by the first signal and/or second signal, which, for example, allow a clinician to listen to sounds relating to blood flow through a blood vessel.

In the illustrated embodiment, the first sensor 122 is attached to the blood flow monitor 160 using a first extension cable 178 and the second sensor 124 is attached to the blood flow monitor 160 using a second extension cable 180. The first extension cable 178 has a first end 182 attached to the first wire member 118 (e.g., first end 142 of the first wire member 118) and a second end 184 attached to the blood flow monitor 160 (e.g., first channel port 170). The second extension cable 180 has a first end 186 attached to the second wire member 120 (e.g., first end 148 of the second wire member 120) and a second end 188 attached to the blood flow monitor 160 (e.g., second channel port 172).

When the blood flow monitor is in the on state, the first visual display field 166 shows the first signal received from the first sensor 122 in graphical form and the second visual display field 168 shows the second signal received from the second sensor 124 in graphical form. The graphical form of the first signal shown in the first visual display field 166 illustrates blood flow through the blood vessel 162. The graphical form of the second signal received from the second sensor 124 shown in the second visual display field 168 illustrates blood flow through the blood vessel 162. The processor 174 receives both the first and second signals, processes the signals, and provides them to a clinician via the first visual display field 166, the second visual display field 168, and/or the speaker 176.

The graphical form of the first signal shown in the first visual display field 166 and the graphical form of the second signal shown in the second visual display field 168 can be presented to a clinician in any suitable format, such as presenting blood flow over time, a sound graphic, and/or a visual representation of blood flow velocity in graphical form. The data provided in a visual display field in graphical form can be shown in real-time, be held or frozen, or a clinician can select a window of time (e.g., adjustable, clinician-defined) within which the clinician would like to review the signal and/or data. Inclusion of the visual display fields 164, 166 is considered advantageous at least because they allow a clinician to review, or monitor, trend data regarding blood flow over time. For example, the first and second visual display fields 164, 166 allow a clinician to review, or monitor, trend data regarding blood flow over time.

As shown in FIGS. 6 and 7, the probe 110 is attached to the blood vessel 162 of a tissue flap 163 such that the first sensor 122 is disposed on a first side 165 of the blood vessel 162 and contacts the blood vessel 162, the second sensor 124 is disposed on the first side 165 of the blood vessel 162 and contacts the blood vessel 162, and the reflector 190 is disposed on a second side 167 of the blood vessel 162 and contacts the blood vessel 162. Depending on the type of reflector included on a retaining member, alternative embodiments can include a reflector that does not contact a blood vessel. The second side 167 of the blood vessel 162 opposably faces the first side 165 of the blood vessel 162. By positioning the cuff 117 in this manner signals from the first sensor 122 can be reflected off of the reflector 190 and be received by the first sensor 122 and/or second sensor 124 and/or signals from the second sensor 124 can be reflected off of the reflector 190 and be received by the first sensor 122 and/or second sensor 124.

Attachment of the cuff 117 to the blood vessel 162 can be accomplished by positioning the cuff 117 in the open configuration on the blood vessel 162 such that the inner surface 134, the first sensor 122, and the second sensor 124 contact the blood vessel 162 and subsequently moving the cuff 117 to the closed position and positioning the clip 140 on the cuff 117. This results in the cuff 117 being attached to the blood vessel 162 and the blood vessel 162 being disposed within passageway 136. In the illustrated embodiment, the cuff 117 is attached to a vein 169 such that the first and second sensors 122, 124 contact the vein 169. However, in alternative embodiments, a retaining member, such as a cuff, can be positioned at any suitable location on, or within, a tissue flap and can be attached to any suitable blood vessel, such as an artery, such that a first sensor and/or a second sensor contacts a portion of the tissue flap (e.g., artery).

As a result of the reflector 190 being positioned on an opposite side of the blood vessel 163, the known distance between the first and second sensors 122, 124, the angle (e.g., approximate angle) of the first sensor and/or second sensor relative to the blood vessel (e.g., blood flow), and/or volumetric flow rate of blood flow through the blood vessel can be calculated using the processor 174. This can be accomplished by the processor 174 calculating a time of flight of one or more ultrasonic signals from a first sensor 122 to a second sensor 124 and/or from a second sensor 124 to a first sensor 122, which are provided to the blood flow monitor 160 via the first and/or second signals and using the first and second channel ports 170, 172 in combination with one another. For example, an accurate determination of volumetric flow rate can be calculated by positioning the first sensor 122 and the second sensor 124 on the cuff 117 at a close proximity to one another and/or by allowing the blood flow monitor 160 (e.g., processor 174) to complete an algorithm to determine the distance between the first and second sensors 122, 124 based on Doppler signaling fundamentals. Furthermore, the inclusion of a reflector 190 that has a variable width allows for a variable signal reflection based on the size of a retaining member, such as a cuff, when positioned on a blood vessel and allows for an accurate determination of the diameter of the blood vessel 162, which further improves the accuracy of any flow rate calculations.

Probes that include a first sensor that monitors blood flow through a blood vessel and creates a first signal, a second sensor that monitors blood flow through a blood vessel and creates a second signal, and a reflector to reflect signals (e.g., ultrasonic signals) from the first sensor and/or second sensor are considered advantageous at least because they allow a blood flow monitor to provide a quantitative indication of blood flow velocity in addition to a qualitative assessment of blood flow velocity, which can include audible and visual indications. In addition, such probes provide for the ability to calculate volumetric flow rate and provide redundancy for the qualitative indication of blood flow in the event that a sensor loses contact with a blood vessel being monitored or otherwise loses the ability to detect blood flow.

Figure 9:
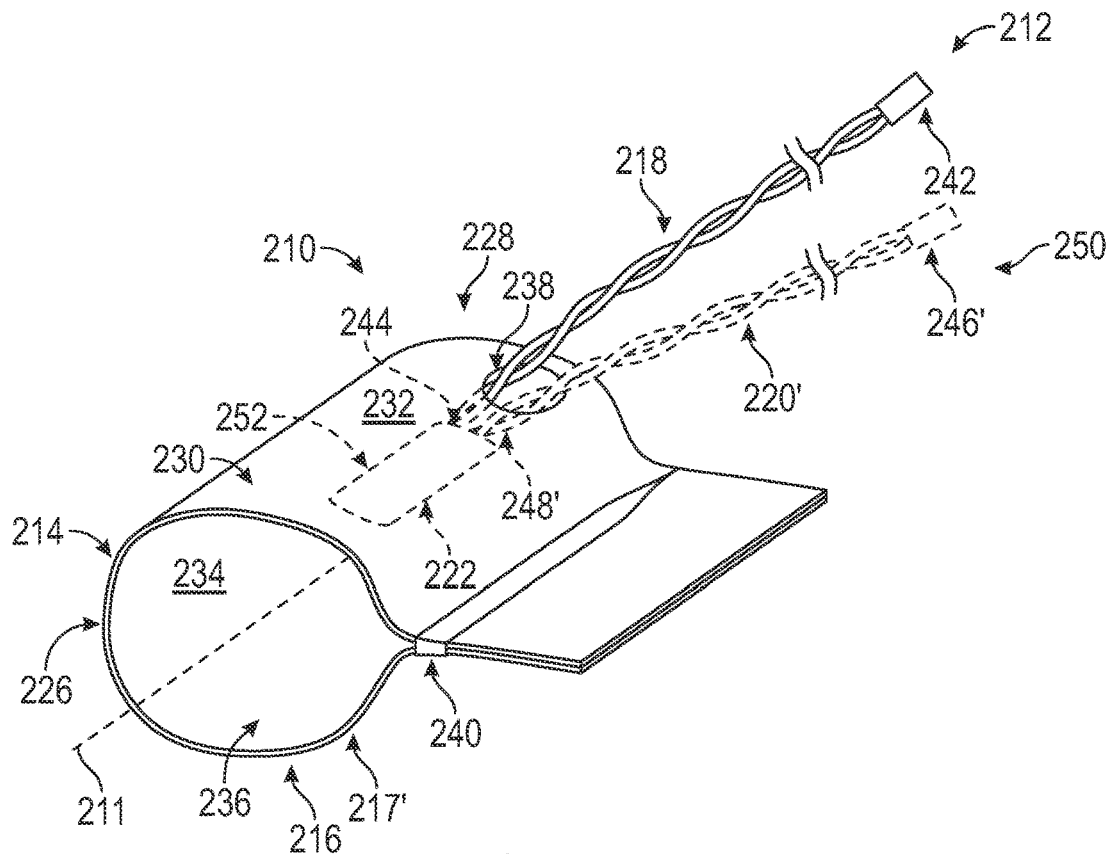
FIG. 9 is a partial perspective view of a third example probe for monitoring blood flow through a blood vessel. The retaining member of the probe is shown in a closed configuration.

FIG. 9 illustrates a third example probe 210 for monitoring blood flow through a blood vessel. The probe 210 has a closed configuration, as shown in FIG. 9, and an open configuration, as described in more detail herein. The probe 210 has a proximal end 212, a distal end 214, and includes a retaining member 216, a first wire member 218, and a first sensor 222.

In the illustrated embodiment, the retaining member 216 is a cuff 217 that is disposed at the distal end 214 of the probe 210 and has a lengthwise axis 211 in the closed configuration, a first end 226, a second end 228, and a main body 230 that defines an outer surface 232, and inner surface 234, a passageway 236, and an opening 238. The cuff 217 includes a clip 240 that can be used to position the cuff 217 in the closed position and to attach to the cuff 217 to a blood vessel.

The first wire member 218 has a first end 242 and a second end 244. The first end 242 of the first wire member 218 is configured to be attached to a blood flow monitor (e.g., via an extension cable) such that signals and/or data can be communicated from the first sensor 222 to the blood flow monitor, and vice versa, during use. The second end 244 of the first wire member 218 is attached to the first sensor 222.

The first sensor 222 is attached to the distal end 214 of the probe 210. The first sensor 222 is positioned such that the first sensor 222 directly contacts a blood vessel when the probe 210 is disposed on a blood vessel. The first sensor 222 is attached to the second end 244 of the first wire member 218 and monitors blood flow through a blood vessel during use. In the illustrated embodiment, the first sensor 222 is releasably attached to the cuff 217 (e.g., inner surface 234). During use, the first sensor 222 provides a first signal that contains blood flow data to a blood flow monitor to which the first sensor 222 is attached via the first wire member 218. The blood flow data relates to the blood flow through the blood vessel to which to probe 210 is attached and the first sensor 222 contacts. In the embodiment shown, the probe 210 is a Doppler probe 250 and the first sensor 222 is a transducer array 252. Examples of transducer arrays considered suitable to include in a probe include piezoelectric micromachined ultrasonic transducers, capacitive micromachined ultrasonic transducers, and any other transducer array considered suitable for a particular embodiment. The elongated portion of the first sensor 222 can be disposed parallel to the lengthwise axis 211 or positioned at an angle relative to the lengthwise axis 211 (e.g., 90 degrees, between about 0 degrees and about 180 degrees).

Alternative embodiments of a probe can include a first wire member 218 and a second wire member 220', as shown in phantom lines in FIG. 9. The first wire member 218 has a first end 242 that is configured to be attached to a first channel port of a blood flow monitor and a second end 244 attached to a first set of sensors within a transducer array 252. The second wire member 220' has a first end 246' that is configured to be attached to a second channel port of a blood flow monitor and a second end 248' attached to the same sensors to which the first wire member 218 is attached or a second, different set of sensors within the transducer array. A processor included in a blood flow monitor can use the signals and/or data received via the first and second channel ports in combination with, or separately from, one another to provide a clinician with information relating to blood flow, as described herein.

Probes that include a transducer array are considered advantageous at least because they can provide signals and/or data to a blood flow monitor that allows for a quantitative indication of blood flow velocity to be provided to a clinician in addition to qualitative audible and visual indications. In addition to the benefits of having multiple sensors as described above, the inclusion of a transducer array provides a mechanism for auto-tuning the signaling to focus on sensors within the array that are receiving the clearest blood flow signals. For example, as a monitor scans an array of sensors, the system can determine which sensors are returning the strongest signals and use those signals, or a portion of those signals, to produce sound and visual outputs. As a result of using only the strongest signals, noise filtering and signal amplification can be accomplished more efficiently. This process can be completed on an ongoing basis such that if blood flow dynamics change the monitor and/or sensor can adjust which sensors to utilize in creating a signal. Optionally, an array of sensors can use beamforming techniques to adjust signal dynamics, accelerating and/or delaying signal transmission and/or receiving to focus a signal on a particular area, or to scan areas that provide the strongest signal. Beamforming also allows adjustment of the signal dynamics to adjust for shape and orientation of the sensor (e.g., making assumptions based on likely positioning of the sensor, then adjusting based on signal processing). Furthermore, the inclusion of an array allows for one or more sensors within the array to emit an ultrasonic signal while one or more other sensors within the array listen, or detect, a reflected signal (e.g., such as those reflected off of a reflector when included on a retaining member), which allows the blood flow monitor to either select certain signals to monitor or combine all signals into one main signal. This improves the overall reliability of the probe and the blood flow monitor. For example, in certain embodiments, a blood flow monitor can include advanced scanning electronics and software to process signals and/or data provided by a sensor (e.g., transducer array) included in a probe and connected to a channel port. This provides a mechanism for scanning more than one sensor on a single channel, which in turn provides a mechanism for the blood flow monitor to monitor two blood vessels with multiple sensors at once (e.g., a first blood vessel via a first channel port and a second blood vessel via a second channel port).

Figure 10:
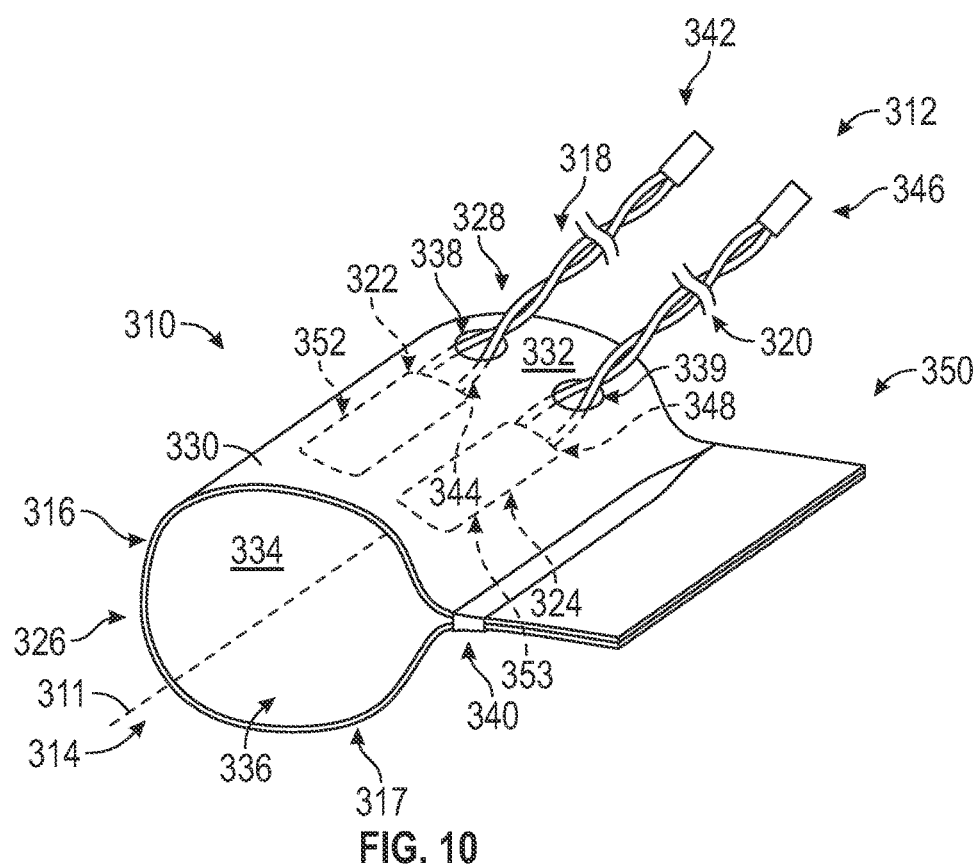
FIG. 10 is a partial perspective view of a fourth example probe for monitoring blood flow through a blood vessel. The retaining member of the probe is shown in a closed configuration.

FIG. 10 illustrates a fourth example probe 310 for monitoring blood flow through a blood vessel. The probe 310 has a closed configuration, as shown in FIG. 10, and an open configuration, as described in more detail herein. The probe 310 has a proximal end 312, a distal end 314, and includes a retaining member 316, a first wire member 318, a second wire member 320, a first sensor 322, and a second sensor 324.

In the illustrated embodiment, the retaining member 316 is a cuff 317 that is disposed at the distal end 314 of the probe 310 and has a lengthwise axis 311 in the closed configuration, a first end 326, a second end 328, and a main body 330 that defines an outer surface 332, and inner surface 334, a passageway 336, a first opening 338, and a second opening 339. The first opening 338 extends from the outer surface 332 to the inner surface 334 and is sized to receive the first wire member 318. The second opening 339 extends from the outer surface 332 to the inner surface 334 and is sized to receive the second wire member 320. The cuff 317 includes a clip 340 that can be used to position the cuff 317 in the closed position and to attach to the cuff 317 to a blood vessel.

The first wire member 318 has a first end 342 and a second end 344. The first end 342 of the first wire member 318 is configured to be attached to a blood flow monitor (e.g., via an extension cable) such that signals and/or data can be communicated from the first sensor 322 to the blood flow monitor, and vice versa, during use. The second end 344 of the first wire member 318 is attached to the first sensor 322. The second wire member 320 has a first end 346 and a second end 348. The first end 346 of the second wire member 320 is configured to be attached to a blood flow monitor (e.g., via an extension cable) such that signals and/or data can be communicated from the second sensor 324 to the blood flow monitor, and vice versa, during use. The second end 348 of the second wire member 320 is attached to the second sensor 324.

The first sensor 322 is attached to the distal end 314 of the probe 310. The first sensor 322 is positioned such that the first sensor 322 directly contacts a blood vessel when the probe 310 is disposed on a blood vessel. The first sensor 322 is attached to the second end 344 of the first wire member 318 and monitors blood flow through a blood vessel during use. In the illustrated embodiment, the first sensor 322 is releasably attached to the cuff 317 (e.g., inner surface 334). During use, the first sensor 322 provides a first signal that contains blood flow data to a blood flow monitor to which the first sensor 322 is attached via the first wire member 318. The blood flow data relates to the blood flow through a blood vessel to which to probe 310 is attached and the first sensor 322 contacts. In the embodiment shown, the probe 310 is a Doppler probe 350 and the first sensor 322 is a transducer array 352.

The second sensor 324 is attached to the distal end 314 of the probe 310. The second sensor 324 is positioned such that the second sensor 324 directly contacts a blood vessel when the probe 310 is disposed on a blood vessel. The second sensor 324 is attached to the second end 348 of the second wire member 320 and monitors blood flow through a blood vessel during use. In the illustrated embodiment, the second sensor 324 is releasably attached to the cuff 317 (e.g., inner surface 334). During use, the second sensor 324 provides a second signal that contains blood flow data to a blood flow monitor to which the second sensor 324 is attached via the second wire member 320. The blood flow data relates to the blood flow through a blood vessel to which to probe 310 is attached and the second sensor 324 contacts. In the embodiment shown, the second sensor 324 is a transducer array 353. A processor included in a blood flow monitor can use the signals and/or data received via the first sensor 322, which can be attached to a first channel port of the blood flow monitor, and the second sensor 324, which can be attached to a second channel port of the blood flow monitor, in combination with, or separately from, one another to provide a clinician with information relating to blood flow, as described herein. Alternatively, a first sensor and a second sensor, each of which comprises a transducer array, can be attached to a single wire member that is attached to a single channel port of a blood flow monitor and can provide signals and/or data to the blood flow monitor, which can process the signals and/or data using a processor, as described herein. The elongated portion of the first sensor 322 and/or second sensor 324 can be disposed parallel to the lengthwise axis 311 or positioned at an angle relative to the lengthwise axis 311 (e.g., 90 degrees, between about 0 degrees and about 180 degrees).

Probes that include a first and second sensors 322, 324 that are transducer arrays are considered advantageous at least because they can provide data to a blood flow monitor that allows for a quantitative indication of blood flow velocity to be provided to a clinician in addition to qualitative audible and visual indications. In addition to the benefits of having multiple sensors as described above, the inclusion of transducer arrays provides a mechanism for auto-tuning the signaling to focus on sensors within the array that are receiving the clearest blood flow signals. Furthermore, the inclusion of first and second sensors 322, 324 that are transducer arrays allow for one or more sensors within each array to emit an ultrasonic signal while one or more other sensors within the first sensor and/or second sensor listen, or detect, a reflected signal (e.g., such as those reflected off of a reflector when included on a retaining member). These signals can be processed by the blood flow monitor such that certain signals are selected to monitor blood flow, or all of the signals can be combined into one main signal. This improves the overall reliability of the probe and the blood flow monitor. For example, in certain embodiments, a blood flow monitor can include advanced scanning electronics and software to allow processing of an array included in a probe connected to a single channel port.

This provides a mechanism for scanning more than one sensor on a single channel, which in turn provides a mechanism for monitoring two blood vessels with multiple sensors at once (e.g., a first blood vessel via the first channel port and a second blood vessel via the second channel port). The inclusion of first and second sensors 322, 324 that are transducer arrays provide redundancy in the event that one sensor loses contact with the blood vessel being monitored and increased signal accuracy.

Various methods of monitoring blood flow through a blood vessel are described herein. While the methods described herein are shown and described as a series of acts, it is to be understood and appreciated that the methods are not limited by the order of acts, as some acts may in accordance with these methods occur in the order shown and/or described, in different orders, concurrently with other acts described herein, or be omitted.

Figure 11:
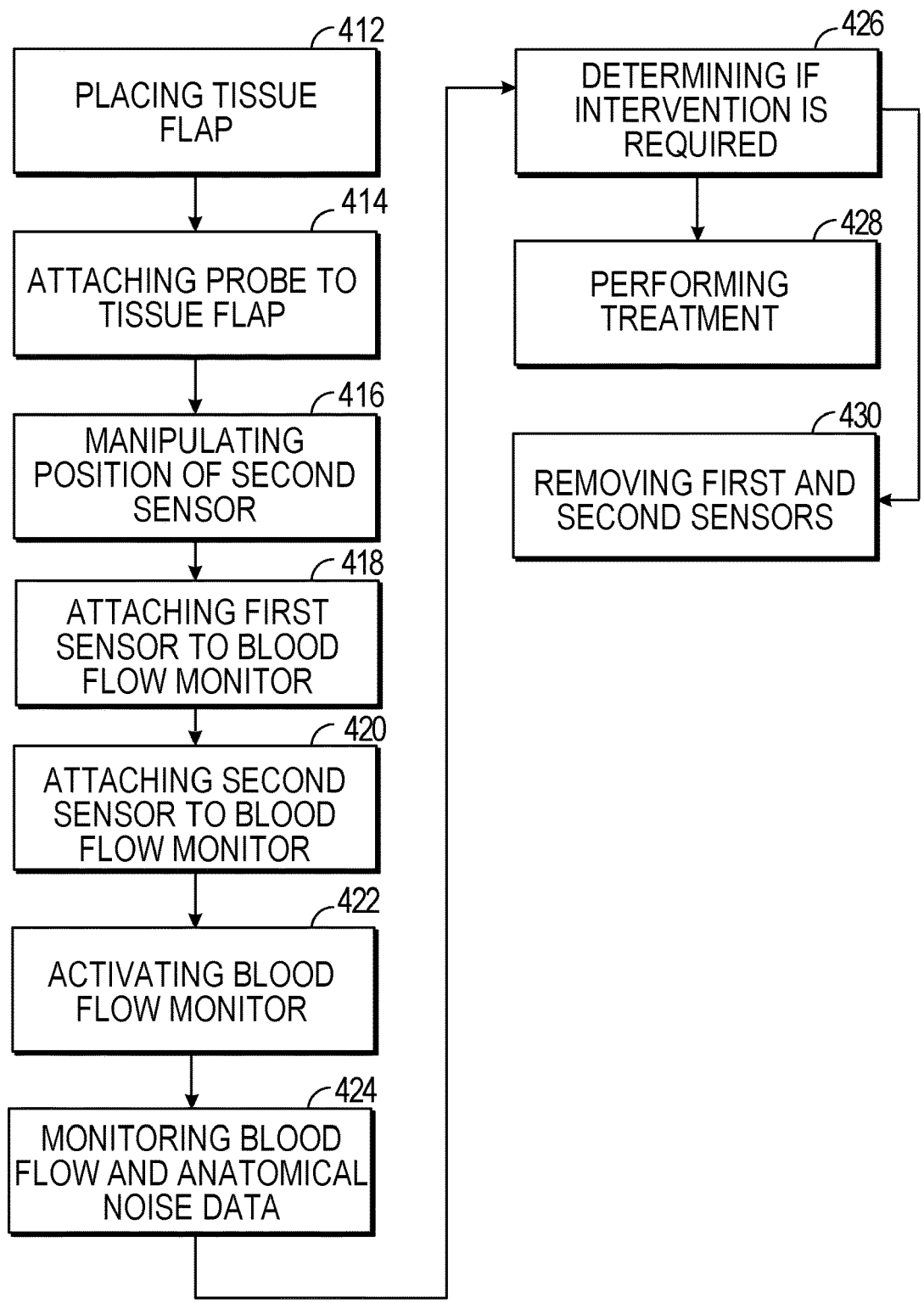
FIG. 11 is a schematic illustration of an example method of monitoring blood flow.

FIG. 11 is a schematic illustration of an example method 410 of monitoring blood flow through a blood vessel.

A step 412 comprises placing a tissue flap at a point of treatment. The tissue flap includes a section of tissue that includes a first blood vessel. Another step 414 comprises attaching a probe to the tissue flap to monitor blood flow through the first blood vessel. The probe includes a retaining member, such as a cuff, a first sensor attached to the retaining member, a first wire member attached to the first sensor, a second sensor attached to the first wire member, and a second wire member attached to the second sensor. The probe is attached to the tissue flap such that the first sensor contacts the first blood vessel and the second sensor is free of contact with the first blood vessel and is disposed within the patient anatomy. Another step 416 comprises manipulating the position of the second sensor on the first wire member such that the second sensor is free of contact with the first blood vessel and is disposed within the patient anatomy. Another step 418 comprises attaching the first sensor to a blood flow monitor that has a first visual display field and a second visual display field. Another step 420 comprises attaching the second sensor to the blood flow monitor. Another step 422 comprises activating the blood flow monitor to observe blood flow data obtained by the first sensor shown in graphical form and anatomical noise data obtained by the second sensor shown in graphical form. Another step 424 comprises monitoring the blood flow data shown in graphical form and the anatomical noise data over a period of time. Another step 426 comprises determining if the blood flow data shown in graphical form indicate intervention is required. If intervention is required, another step 428 comprises performing treatment. If intervention is not required, another step 430 comprises removing the first sensor from the tissue flap and removing the second sensor from the first wire member.

Step 412 can be accomplished by placing the tissue flap at any suitable point of treatment and selection of a suitable point of treatment can be based on various considerations, such as the treatment intended to be performed. Examples of points of treatment considered suitable to place a tissue flap include the head (e.g., face), neck, chest, breast, back, abdomen, arms, buttocks, legs (e.g., thighs), areas of a body that previously included defects, such as those from an injury or other surgery (e.g., mastectomy), and any other point of treatment considered suitable for a particular embodiment.

A tissue flap utilized in a method of monitoring blood flow through a blood vessel can comprise any suitable section of tissue that can be used to complete an autologous tissue reconstruction procedure, includes at least one blood vessel, and/or that has been moved from a donor site of a patient to a recipient site of the patient. Alternatively, a method of monitoring blood flow through a blood vessel can be completed on an organ. Examples of tissue flaps considered suitable to complete a method of monitoring blood flow through a blood vessel include local flaps (e.g., advancement flaps, rotation flaps, transposition flaps, interpolation flaps), free flaps, transverse rectus abdominis muscle flaps, deep inferior epigastric perforator flaps, latissimus dorsi flaps, gluteal artery perforator flaps, transverse upper gracilis flaps, flaps obtained from the chest, breast, back, abdomen, arms, buttocks, or legs (e.g., thighs) of a patient, combinations of those described herein, and any other tissue flap considered suitable for a particular embodiment.

Step 414 can be accomplished by attaching any suitable probe to the tissue flap such that the first sensor of the probe contacts the first blood vessel. Examples of probes considered suitable to attach to a blood vessel include probe 10 illustrated in FIGS. 1, 2, and 3, the probes described herein, and any other probe considered suitable for a particular embodiment. FIG. 2 illustrates probe 10 attached to a first blood vessel 62 of a tissue flap 63. The first sensor 22 is positioned such that it contacts the first blood vessel 62 (e.g., the first sensor 22 directly contacts the first blood vessel 62). The probe 10 is attached to the first blood vessel 62 by wrapping the retaining member 16 (e.g., cuff 17) around the first blood vessel 62 and attaching the retaining member 16 directly to the first blood vessel 62 (e.g., surgically) using a clip 40. The first sensor 22 allows for monitoring of blood flow within the first blood vessel 62 intraoperatively and postoperatively following completion of a procedure (e.g., reconstructive procedure).

While the probe 10 has been illustrated as including various components and as being attached to the first blood vessel 62 in a particular manner, a probe can include any suitable number of components and be attached to a blood vessel in any suitable manner. Selection of a suitable number of components for a probe to include and of a suitable method or technique to attach a sensor to a blood vessel can be based on various considerations, including the material forming the probe and/or the size and/or location of the blood vessel.

Step 416 can be accomplished by applying a force on the second sensor directed proximally along the first wire member, distally along the first wire member, and/or around the circumference of the first wire member. Step 416 can be used to position the second sensor in a desired location within the patient anatomy where anatomical background noise can be obtained by the second sensor. Optionally, step 416 can be omitted from method 410 in embodiments in which the second sensor is pre-attached to a first wire member and/or is positioned in a desired location along the length of the first wire member.

Step 418 can be accomplished by attaching the first sensor to any suitable blood flow monitor that has a first visual display field and a second visual display field. FIG. 3 illustrates an example blood flow monitor 60 considered suitable to attach the first sensor 22 illustrated in FIGS. 1 and 2. In the illustrated embodiment, the first sensor 22 is attached to the blood flow monitor 60 using a first extension cable 78 that has a first end 82 attached to the first sensor 22 and a second end 84 attached to the blood flow monitor 60 (e.g., first channel port 70). However, in alternative embodiments, a first sensor can be attached directly to a blood flow monitor without using an extension cable. In an alternative embodiment, step 418 can comprise attaching the first sensor to a blood flow monitor that has a first visual display field.

Step 420 can be accomplished by attaching the second sensor to the blood flow monitor to which the first sensor is attached. FIG. 3 illustrates the second sensor 24 attached to the blood flow monitor 60 using a second extension cable 80 that has a first end 86 attached to the second sensor 24 and a second end 88 attached to the blood flow monitor 60 (e.g., second channel port 72). However, in alternative embodiments, a second sensor can be attached directly to a blood flow monitor without using an extension cable.

Step 422 can be accomplished by moving the blood flow monitor from an off state to an on state to observe the blood flow data relating to the first blood vessel obtained by the first sensor and shown in graphical form and to observe anatomical noise data relating to the patient obtained by the second sensor and shown in graphical form. FIG. 3 illustrates a first visual display field 66 and a second visual display field 68. When the blood flow monitor is in the on state, the first visual display field 66 can show blood flow data relating to blood flow for the first blood vessel 62 and obtained by the first sensor 22 in graphical form (e.g., sound data from first sensor in graphical form). When the blood flow monitor is in the on state, the second visual display field 68 can show anatomical noise data relating to anatomical noise and obtained from the second sensor 24 in graphical form. When activated, the blood flow monitor obtains the first signal and the second signal, removes the anatomical noise data obtained from the second signal from the anatomical noise data obtained by the first signal, and creates an adjusted first signal containing blood flow data from the first signal. The adjusted first signal can be shown in graphical form on the first visual display field 66 and/or provided audibly via the speaker. The processor 74 of the blood flow monitor 60 can automatically, or upon direction by a clinician, remove the anatomical noise data received from the second sensor 24 from the first signal received from the first sensor 22 resulting in the adjusted first signal that includes only blood flow data, or blood flow data and a portion of the anatomical noise data of the first signal, which can be displayed in graphical form in single or combined visual display field. In an alternative embodiment, step 422 comprises activating the blood flow monitor to observe blood flow data obtained by the first sensor shown in graphical form and/or provided audibly via the speaker. In a further alternative embodiment, step 422 comprises activating the blood flow monitor to observe an adjusted first signal shown in graphical form and/or provided audibly via the speaker. The number and type of data shown in graphical form by a blood flow monitor can vary depending on the type of blood flow monitor being used to complete a method of monitoring blood flow.

Inclusion of the visual display fields 66, 68 is considered advantageous at least because they allow a clinician to review, or monitor, trend data regarding blood flow over time. For example, the first visual display field 66 allows a clinician to review, or monitor, trend data regarding blood flow over time and the second visual display field 68 allows the clinician to review, or monitor, data relating to anatomical noise. In addition, a blood flow monitor can include functionality for holding maximum values and/or spectrum data over a clinician-defined window of time and/or for storing data and associated sounds before a signal loss.

Step 424 can be accomplished using the blood flow monitor and by maintaining the blood flow monitor in the on state such that blood flow data received from the first sensor and anatomical noise data received from the second sensor can be recorded, adjusted, and/or provided to a clinician. Alternatively, step 424 comprises monitoring the blood flow data shown in graphical form, the adjusted first signal shown in graphical form, and/or the blood flow data shown in graphical form and/or adjust first signal provided audibly via the speaker. This alternative step can be accomplished using the blood flow monitor and by maintaining the blood flow monitor in the on state such that blood flow data received from the first sensor and/or second signal and/or anatomical noise data can be recorded, adjusted, and/or provided to a clinician.

A blood flow monitor can be maintained in the on state for any suitable period of time and selection of a suitable period of time can be based on various considerations, such as the location of the implant site of a tissue flap and/or the type of tissue flap that has been implanted. Examples of periods of time considered suitable to maintain a blood flow monitor in an on state to monitor blood flow through a blood vessel of a tissue flap and/or anatomical noise data include one or more seconds, one or more minutes, one or more hours, one or more days, one or more weeks, and any other period of time considered suitable for a particular embodiment. For example, a blood flow monitor can be maintained in an on state to monitor blood flow through a blood vessel of a tissue flap and/or anatomical noise for about 24 hours, about 48 hours, about 72 hours, and any other period of time considered suitable for a particular embodiment.

While the first and second visual display fields 66, 68 can display particular data in graphical form, a visual display field can display any suitable data in graphical form and selection of suitable data to display on a visual display field in graphical form can be based on various considerations, including the data desired by a clinician relating to an implanted tissue flap. Examples of data considered suitable to display on a visual display field in graphical form include data relating to blood flow of a blood vessel included in a tissue flap, anatomical noise data, tissue health, tissue oxygenation saturation levels, temperature, blood pressure, data over a period of time, clinician-defined data, data obtained by a clinician (e.g., data relating to one or more of the color, the temperature, the capillary refill time, any blood loss, edema, and/or appearance of the flap) that can be displayed as data and/or a photograph, combinations of the data described herein, and any other data considered suitable for a particular embodiment. Any signal and/or data described herein can be stored and utilized throughout a procedure using a storage device included in a blood flow monitor.

A speaker included in a blood flow monitor can emit any suitable sound, such as Doppler sounds provided by a first sensor (e.g., first signal) to allow a clinician to listen to sounds relating to historical and/or current blood flow through a blood vessel of a tissue flap. In addition, a speaker included in a blood flow monitor can emit sounds provided by a second sensor (e.g., second signal) to allow a clinician to listen to sounds relating to historical and/or current anatomical noise within the anatomy of a patient. A blood flow monitor can provided various alerts to provide feedback to a clinician, such as sound alerts associated with clinician-defined settings, clinician-defined trigger points (e.g., change in sound, change in a device event, change in sensor readings), alerts relating to a pre-defined sensor reading, alerts relating to a pre-defined volumetric flow rates, alters relating to the status of the blood flow monitor (e.g., in off state, lost power, malfunctioning), and any other alert considered suitable for a particular embodiment.

Step 426 can be accomplished by reviewing the data provided in the first visual display field, the second visual display field, and/or by listening to sounds emitted from a speaker included in the blood flow monitor to determine whether any of the data and/or sounds indicate that the tissue flap requires intervention. For example, if the data displayed in a visual display field (e.g., blood flow, anatomical noise data) indicate that a variable (e.g., blood flow) is below a threshold (e.g., clinician-defined), intervention is required. Alternatively, if the data displayed in a visual display field (e.g., blood flow over time, anatomical noise data) indicate that a variable is above the threshold, intervention is not required.

If intervention is required, step 428 can be accomplished by performing any suitable treatment to accomplish the intervention. Examples of treatments considered suitable to accomplish intervention include repositioning a sensor (e.g., first sensor, second sensor), replacing an implanted tissue flap with a second tissue flap, repositioning the patient, correcting a kink, twist, or tension on a vessel, correcting the design of the anastomosis, treating infection, clot extraction, administering one or more drugs (e.g., anticoagulants, blood thinners), increasing blood pressure, combinations of the treatments described herein, and any other treatment considered suitable for a particular embodiment. If intervention is not required, or if intervention has been completed (e.g., via step 428), step 430 can be accomplished by removing the first sensor from the first blood vessel of the tissue flap and removing the second sensor from the first wire member. Optionally, depending on the placement of the first and second wire members, step 430 can also comprise removing the first and second wire members from the anatomy of the patient and/or omitting the step of removing the second sensor from the first wire member. Removal of the first sensor can be accomplished by removing any sutures and/or tape from the first wire member outside of the body of the patient and applying an axial force on the first wire member near the sensor (e.g., crystal) and away from the patient to disengage the sensor (e.g., crystal) from the retaining member. The retaining member can optionally be left in place around the blood vessel and any opening can be closed (e.g., using sutures). Removal of the second sensor can be accomplished by removing any sutures and/or tape from the second wire member outside of the body of the patient and applying an axial force on the second wire member near the sensor (e.g., crystal) and away from the patient to disengage the sensor (e.g., crystal) from the first wire member. Optionally, the second sensor can be left attached to the first wire member and removed along with the first sensor and first wire member.

In alternative embodiments, and depending on the type of sensors being used to provide data to a blood flow monitor, step 426, step 428, and/or step 430 can be omitted from method 410. Step 430 can be omitted, for example, in instances in which the first and second sensors are biodegradable and/or provide data to a blood flow monitor wirelessly. In these embodiments, the first and second wire member can be removed by removing any sutures and/or tape from the wire member outside of the body of the patient and applying an axial force on the wire member and away from the patient to disengage the wire member from the sensor. An optional step comprises deactivating the blood flow monitor, which can be accomplished by moving the blood flow monitor from the on state to the off state.

Figure 12:
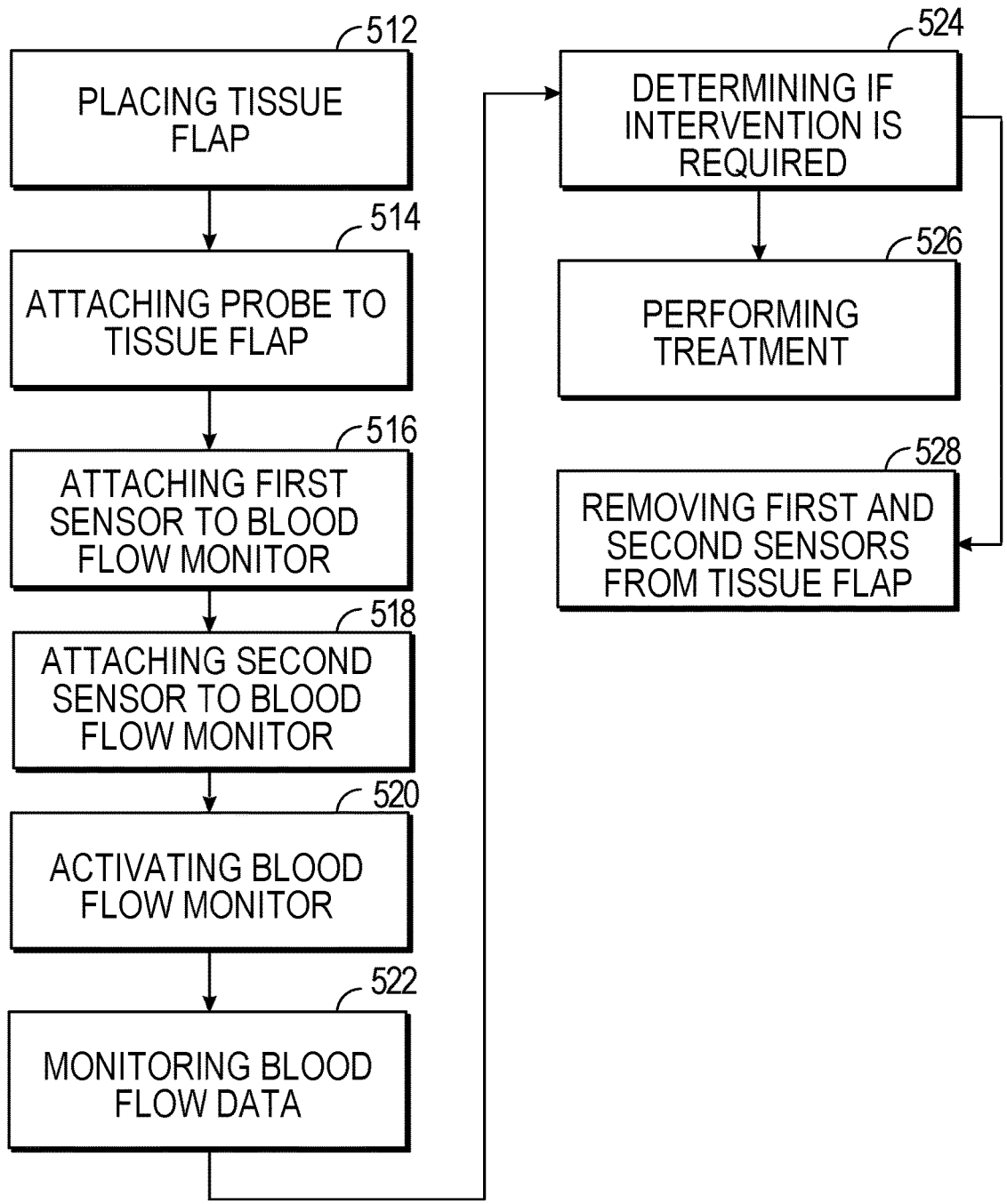
FIG. 12 is a schematic illustration of another example method of monitoring blood flow.

FIG. 12 is another schematic illustration of an example method 510 of monitoring blood flow through a blood vessel.

A step 512 comprises placing a tissue flap at a point of treatment. The tissue flap includes a section of tissue that includes a first blood vessel. Another step 514 comprises attaching a probe to the tissue flap to monitor blood flow through the first blood vessel. The probe includes a retaining member, such as a cuff, a first wire member, a first sensor attached to the first wire member and the retaining member, a second wire member, a second sensor attached to the retaining member and the second wire member, and a reflector. The probe is attached to the tissue flap such that the first sensor and the second sensor contact the first blood vessel. Another step 516 comprises attaching the first sensor to a blood flow monitor that has a first visual display field and a second visual display field. Another step 518 comprises attaching the second sensor to the blood flow monitor. Another step 520 comprises activating the blood flow monitor to observe blood flow data obtained by the first sensor shown in graphical form and blood flow data obtained by the second sensor shown in graphical form. Another step 522 comprises monitoring the blood flow data shown in graphical form over a period of time. Another step 524 comprises determining if the blood flow data shown in graphical form indicates intervention is required. If intervention is required, another step 526 comprises performing treatment. If intervention is not required, another step 528 comprises removing the first sensor and the second sensor from the tissue flap.

Step 512 can be accomplished as described herein with respect to step 412.

Step 514 can be accomplished by attaching any suitable probe to the tissue flap such that the first sensor and the second sensor of the probe contact the first blood vessel. Examples of probes considered suitable to attach to a blood vessel include probe 110 illustrated in FIGS. 4, 5, 6, 7, and 8, the probes described herein, and any other probe considered suitable for a particular embodiment. FIGS. 6 and 7 illustrate probe 110 attached to a first blood vessel 162 of a tissue flap 163. The first sensor 122 contacts the first blood vessel 162 (e.g., the first sensor 122 directly contacts the first blood vessel 162) and the second sensor 124 contacts the first blood vessel 162 (e.g., the second sensor 124 directly contacts the first blood vessel 162). The probe 110 is attached to the first blood vessel 162 by wrapping the retaining member 116 (e.g., cuff 117) around the first blood vessel 162 and attaching the retaining member 116 directly to the first blood vessel 162 (e.g., surgically) using a clip 140. The first sensor 122 and the second sensor 124 allow for monitoring of blood flow within the first blood vessel 162 intraoperatively and postoperatively following completion of a procedure (e.g., reconstructive procedure). In the illustrated embodiment, the first sensor 122 and the second sensor 124 are disposed deep within the tissue flap 163 (i.e., beneath a surface of the flap 163, subcutaneously) and are attached to a vein 169.

Step 516 can be accomplished by attaching the first sensor to any suitable blood flow monitor that has a first visual display field and a second visual display field. FIG. 8 illustrates an example blood flow monitor 160 considered suitable to attach the first sensor 122 illustrated in FIGS. 4, 5, and 7. In the illustrated embodiment, the first sensor 122 is attached to the blood flow monitor 160 using a first extension cable 178 that has a first end 182 attached to the first sensor 122 and a second end 184 attached to the blood flow monitor 160 (e.g., first channel port 170).

Step 518 can be accomplished by attaching the second sensor to the blood flow monitor to which the first sensor is attached. FIG. 8 illustrates the second sensor 124 attached to the blood flow monitor 160 using a second extension cable 180 that has a first end 186 attached to the second sensor 124 and a second end 188 attached to the blood flow monitor 160 (e.g., second channel port 172).

Step 520 can be accomplished by moving the blood flow monitor from an off state to an on state to observe the blood flow data relating to the first blood vessel obtained by the first sensor and shown in graphical form and to observe blood flow data relating to the first blood vessel obtained by the second sensor and shown in graphical form. FIG. 8 illustrates a first visual display field 166 and a second visual display field 168. When the blood flow monitor is in the on state, the first visual display field 166 can show blood flow data relating to blood flow through the first blood vessel 162 and obtained by the first sensor 122 in graphical form (e.g., sound data from first sensor 122 in graphical form). When the blood flow monitor is in the on state, the second visual display field 168 can show blood flow data received relating to blood flow through the first blood vessel 162 and obtained from the second sensor 124 in graphical form (e.g., sound data from second sensor 124 in graphical form). The inclusion of the reflector 190 provides a mechanism for the first sensor 122 and/or second sensor 124 to provide additional data to the processor 174, as described herein (e.g., data relating to signals sent from the first sensor 122 and received by the first sensor 122 and/or second sensor 124 and/or data relating to signals sent from the second sensor 124 and received by the first sensor 122 and/or second sensor 124). The processor 174 can automatically, or upon direction by a clinician, use this additional data to produce graphical forms of the additional data on the first visual display field 166 and/or second visual display field 168. The additional data can relate to distances between the first and second sensors 122, 124, volumetric flow rate of blood flow through a blood vessel (e.g., first blood vessel), a diameter of the blood vessel, and any other data received from the first sensor 122 and/or second sensor 124.

Inclusion of the visual display fields 166, 168 is considered advantageous at least because they allow a clinician to review, or monitor, trend data regarding blood flow over time. For example, the first visual display field 166 allows a clinician to review, or monitor, trend data regarding blood flow over time and the second visual display field 168 allows the clinician to review, or monitor, data relating to blood flow over time. In addition, a blood flow monitor can include functionality for holding maximum values and/or spectrum data over a clinician-defined window of time and/or for storing data and associated sounds before a signal loss.

While the visual display fields 166, 168 can display blood flow data in graphical form, alternative embodiments can allow a clinician to change what is being displayed on a visual display field. For example, a blood flow monitor can optionally include a switch that allows a clinician to manipulate what is being displayed on a visual display field. Examples of data represented in graphical form that can be displayed on a visual display field include distances between first and second sensors, volumetric flow rate of blood flow through a blood vessel (e.g., first blood vessel), a diameter of the blood vessel, and any other data represented in graphical form.

Step 522 can be accomplished using the blood flow monitor and by maintaining the blood flow monitor in the on state such that blood flow data received from the first sensor and blood flow data received from the second sensor can be recorded, adjusted, and/or provided to a clinician.

Step 524 can be accomplished by reviewing the data provided in the first visual display field, the second visual display field, and/or by listening to sounds emitted from a speaker included in the blood flow monitor to determine whether any of the data and/or sounds indicate that the tissue flap requires intervention. For example, if the data displayed in a visual display field (e.g., blood flow) indicate that a variable (e.g., blood flow) is below a threshold (e.g., clinician-defined), intervention is required. Alternatively, if the data displayed in a visual display field (e.g., blood flow over time, anatomical noise data) indicate that a variable is above the threshold, intervention is not required.

Step 526 can be accomplished as described herein with respect to step 428.

If intervention is not required, or if intervention has been completed (e.g., via step 526), step 528 can be accomplished by removing the first sensor from the first blood vessel of the tissue flap and removing the second sensor from the first blood vessel of the tissue flap. Removal of the first sensor can be accomplished by removing any sutures and/or tape from the first wire member outside of the body of the patient and applying an axial force on the first wire member near the first sensor and away from the patient to disengage the first sensor from the retaining member. Removal of the second sensor can be accomplished by removing any sutures and/or tape from the second wire member outside of the body of the patient and applying an axial force on the second wire member near the second sensor and away from the patient to disengage the second sensor from the retaining member. The retaining member can optionally be left in place around the blood vessel or removed and any opening can be closed (e.g., using sutures).

In alternative embodiments, and depending on the type of sensor being used to provide data to a blood flow monitor, step 524, step 526, and/or step 528 can be omitted from method 510.

Figure 13:
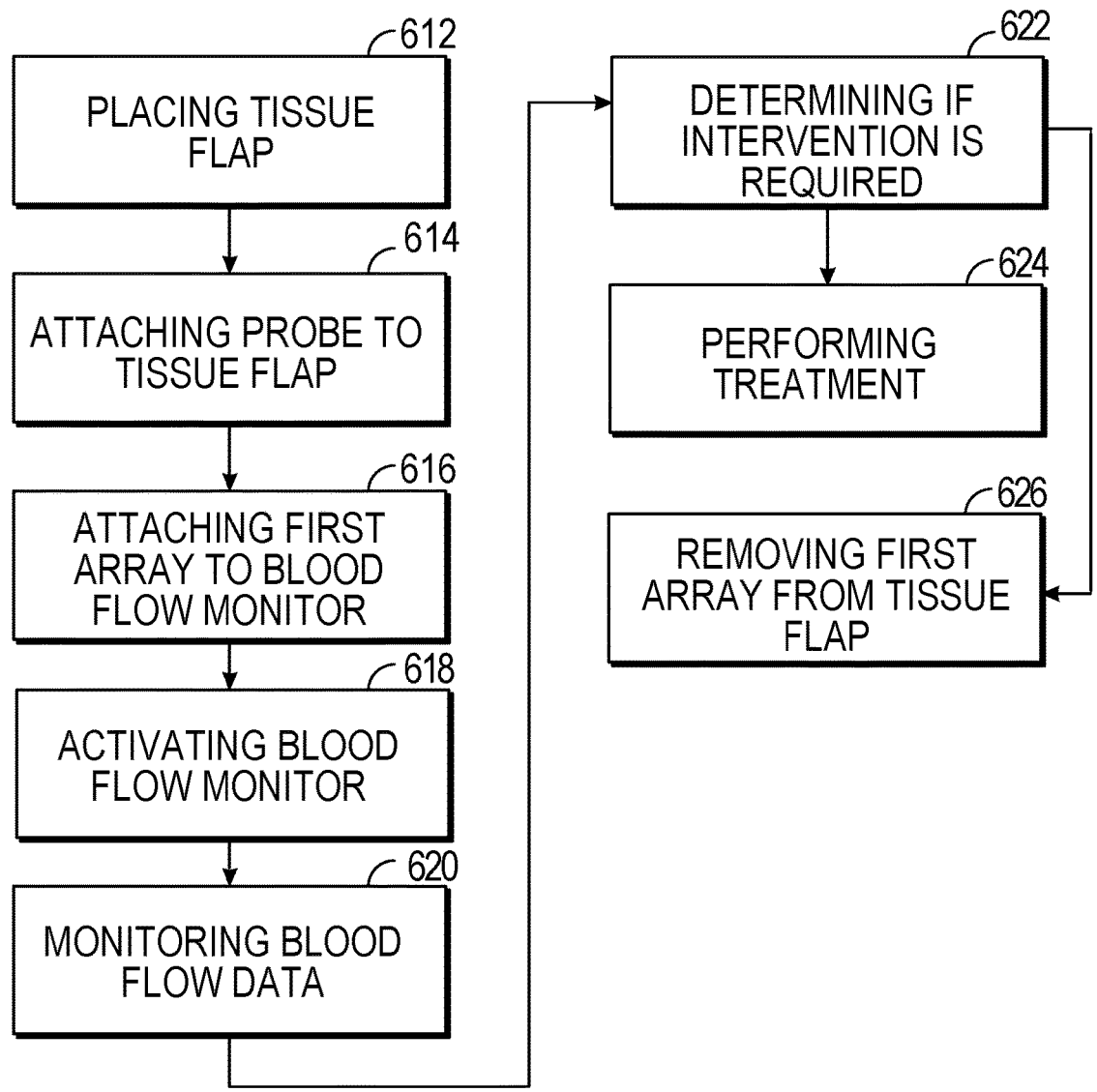
FIG. 13 is a schematic illustration of another example method of monitoring blood flow.

FIG. 13 is another schematic illustration of an example method 610 of monitoring blood flow through a blood vessel.

A step 612 comprises placing a tissue flap at a point of treatment. The tissue flap includes a section of tissue that includes a first blood vessel. Another step 614 comprises attaching a probe to the tissue flap to monitor blood flow through the first blood vessel. The probe includes a retaining member, such as a cuff, a first transducer array attached to the retaining member, and a first wire member attached to the first transducer array. The probe is attached to the tissue flap such that the first transducer array contacts the first blood vessel. Another step 616 comprises attaching the first transducer array to a blood flow monitor that has a first visual display field. Another step 618 comprises activating the blood flow monitor to observe blood flow data obtained by the first sensor shown in graphical form. Another step 620 comprises monitoring the blood flow data shown in graphical form over a period of time. Another step 622 comprises determining if the blood flow data shown in graphical form indicate intervention is required. If intervention is required, another step 624 comprises performing treatment. If intervention is not required, another step 626 comprises removing the first transducer array from the tissue flap.

Step 612 can be accomplished as described herein with respect to step 412.

Step 614 can be accomplished by attaching any suitable probe to the tissue flap such that the first transducer array of the probe contacts the first blood vessel. Examples of probes considered suitable to attach to a blood vessel include probe 210 illustrated in FIG. 9, probe 310 illustrated in FIG. 10, the probes described herein, and any other probe considered suitable for a particular embodiment. In embodiments in which probe 210 is used to complete method 610, the probe 210 is attached to the first blood vessel such that the first transducer array 252 contacts the first blood vessel (e.g., the first transducer array 252 directly contacts the first blood vessel). The probe 210 is attached to the first blood vessel by wrapping the retaining member 216 around the first blood vessel and attaching the retaining member 216 directly to the first blood vessel (e.g., surgically) using a clip 240. The first transducer array 252 allows for monitoring of blood flow within the first blood vessel intraoperatively and postoperatively following completion of a procedure (e.g., reconstructive procedure).

In embodiments in which probe 310 is used to complete method 610, step 614 comprises attaching a probe to the tissue flap to monitor blood flow through the first blood vessel. The probe includes a retaining member, such as a cuff, a first transducer array attached to the retaining member, a first wire member attached to the first transducer array, a second transducer array attached to the retaining member, and a second wire member attached to the second transducer array. The probe 310 is attached to the tissue flap such that the first transducer array 352 and the second transducer array 353 contact the first blood vessel (e.g., the first transducer array 352 and the second transducer array 353 directly contact the first blood vessel). The probe 310 is attached to the first blood vessel by wrapping the retaining member 316 around the first blood vessel and attaching the retaining member 316 directly to the first blood vessel (e.g., surgically) using a clip 340. The first transducer array 352 and the second transducer array 353 allow for monitoring of blood flow within the first blood vessel intraoperatively and postoperatively following completion of a procedure (e.g., reconstructive procedure).

Step 616 can be accomplished by attaching the first sensor to any suitable blood flow monitor that has a first visual display field. In embodiments in which probe 210 is used to complete method 610, the first transducer array 252 can be attached to a blood flow monitor using a first extension cable that has a first end attached to the first transducer array 252 and a second end attached to the blood flow monitor (e.g., first channel port).

In embodiments in which probe 310 is used to complete method 610, step 616 can be accomplished by attaching the first transducer array 352 to a blood flow monitor that has a first visual display field and a second visual display field. The first transducer array 352 can be attached to the blood flow monitor using a first extension cable that has a first end attached to the first transducer array 352 and a second end attached to the blood flow monitor (e.g., first channel port). Another step that would be completed in embodiments in which probe 310 is used to complete method 610 includes attaching a second transducer array to the blood flow monitor to which the first transducer array is attached. The second transducer array 353 can be attached to the blood flow monitor using a second extension cable that has a first end attached to the second transducer array 353 and a second end attached to the blood flow monitor (e.g., second channel port).

Step 618 can be accomplished by moving the blood flow monitor from an off state to an on state to observe the blood flow data relating to the first blood vessel obtained by the first transducer array and shown in graphical form on the first visual display field (e.g., sound data from first sensor in graphical form). In embodiments in which probe 310 is used to complete method 610, step 618 can be accomplished by moving the blood flow monitor from an off state to an on state to observe the blood flow data relating to the first blood vessel obtained by the first transducer array and shown in graphical form on the first visual display field (e.g., sound data from first sensor in graphical form) and to observe the blood flow data relating to the first blood vessel obtained by the second transducer array and shown in graphical form on the second visual display field (e.g., sound data from second sensor in graphical form).

Step 620 can be accomplished using the blood flow monitor and by maintaining the blood flow monitor in the on state such that data received from the first transducer array relating to the blood flow through the first blood vessel can be recorded, adjusted, and/or provided to a clinician. In embodiments in which probe 310 is used to complete method 610, step 620 can be accomplished using the blood flow monitor and by maintaining the blood flow monitor in the on state such that data received from the first transducer array relating to the blood flow through the first blood vessel and the second transducer array relating to the blood flow through the first blood vessel can be recorded, adjusted, and/or provided to a clinician.

Step 622 can be accomplished by reviewing the data provided in the first visual display field and/or by listening to sounds emitted from a speaker included in the blood flow monitor to determine whether any of the data and/or sounds indicate that the tissue flap requires intervention. In embodiments in which probe 310 is used to complete method 610, Step 622 can be accomplished by reviewing the data provided in the first visual display field and/or the second visual display field to determine whether any of the data indicate that the tissue flap requires intervention.

If intervention is required, step 624 can be accomplished as described herein with respect to step 428.

If intervention is not required, or if intervention has been completed (e.g., via step 624), step 626 can be accomplished by removing the first transducer array from the first blood vessel of the tissue flap. Removal of the first transducer array can be accomplished by removing any sutures and/or tape from the first wire member outside of the body of the patient and applying an axial force on the first wire member near the transducer array and away from the patient to disengage the first transducer array from the retaining member. The retaining member can optionally be left in place around the blood vessel and any opening can be closed (e.g., using sutures).

In embodiments in which probe 310 is used to complete method 610, if intervention is not required, or if intervention has been completed (e.g., via step 624), step 626 can be accomplished by removing the first transducer array from the first blood vessel of the tissue flap and removing the second transducer array from the tissue flap. Removal of the first transducer array can be accomplished by removing any sutures and/or tape from the first wire member outside of the body of the patient and applying an axial force on the first wire member near the first transducer array and away from the patient to disengage the first transducer array from the retaining member. Removal of the second transducer array can be accomplished by removing any sutures and/or tape from the second wire member outside of the body of the patient and applying an axial force on the second wire member near the second transducer array and away from the patient to disengage the second transducer array from the retaining member. The retaining member can optionally be left in place around the blood vessel and any opening can be closed (e.g., using sutures).

In alternative embodiments, and depending on the type of sensor being used to provide data to a blood flow monitor, step 622, step 624, and/or step 626 can be omitted from method 610. An optional step comprises deactivating the blood flow monitor, which can be accomplished by moving the blood flow monitor from the on state to the off state.

The methods of monitoring blood flow described herein are considered advantageous at least because they provide graphic visualizations of the data being provided by a first sensor and/or second sensor on a visual display field and/or sounds provided by the first signal and/or second signal. For example, a clinician visualizing blood flow data presented in graphical form on a visual display field and/or listening to sounds provided by a blood flow monitor can determine whether there is a positive or stable trend, which could indicate there is adequate blood flow, or if there is a negative or abrupt trend, which could indicate that further inspection of the treatment area is needed. Furthermore, a temporary negative trend could indicate that the blood pressure of the patient is going down or the vessel is dilating due to the swelling going down at the site. Alternatively, a trend could also indicate whether a brief interruption in the signal may be attributed to a collapsed vessel due to patient movement or a sensor becoming dislodged from the tissue. By monitoring the data, graphics, and/or trend data provided on a blood flow monitor during, or subsequent to a procedure, unnecessary intervention associated with false positives and tissue flap loss associated with false negatives can be prevented.

Those with ordinary skill in the art will appreciate that various modifications and alternatives for the described and illustrated embodiments can be developed in light of the overall teachings of the disclosure, and that the various elements and features of one example described and illustrated herein can be combined with various elements and features of another example without departing from the scope of the invention. Accordingly, the particular arrangement of elements and steps disclosed herein have been selected by the inventor(s) simply to describe and illustrate examples of the invention and are not intended to limit the scope of the invention or its protection, which is to be given the full breadth of the appended claims and any and all equivalents thereof.

What is claimed is:

1. A probe for monitoring blood flow through a blood vessel, the probe comprising:
    a retaining member having a main body defining an outer surface and an inner surface, the retaining member moveable between an open configuration and a closed configuration, the inner surface defining a passageway in the closed configuration;
    a first sensor disposed on the inner surface of the retaining member;
    a first wire member attached to the first sensor and having a first end and a second end;
    a second sensor disposed on the first wire member between the first end and the second end of the first wire member; and
    a second wire member attached to the second sensor.

2. The probe of claim 1, wherein the retaining member defines an opening that extends from the inner surface to the outer surface; and
    wherein the first wire member is disposed through the opening.

3. The probe of claim 2, wherein the second sensor is disposed on the first wire member between the retaining member and the first end of the first wire member.

4. The probe of claim 1, wherein the second sensor is disposed on the first wire member a distance from the first sensor between about 5 millimeters and about 15 millimeters.

5. The probe of claim 1, wherein said probe has a proximal end, a distal end, and a length extending from the proximal end to the distal end; and
    wherein the second sensor is disposed a distance from the distal end of the probe that is less than 50% of the length of the probe.

6. The probe of claim 1, wherein the second sensor is free of attachment to the retaining member.

7. The probe of claim 1, wherein the first sensor is a transducer; and
    wherein the second sensor is a transducer.

8. The probe of claim 1, wherein the first sensor is releasably attached to the retaining member.

9. The probe of claim 1, wherein the second sensor is releasably attached to the first wire member.

10. A blood flow monitoring system for monitoring blood flow through a blood vessel, the system comprising:
    a probe comprising:
        a retaining member having a main body defining an outer surface and an inner surface, the retaining member moveable between an open configuration and a closed configuration, the inner surface defining a passageway in the closed configuration;
        a first sensor disposed on the inner surface of the retaining member and providing a first signal containing blood flow data and anatomical noise data;
        a first wire member attached to the first sensor and having a first end and a second end;
        a second sensor disposed on the first wire member between the first end and the second end of the first wire member, the second sensor providing a second signal containing anatomical noise data; and
        a second wire member attached to the second sensor;
    a blood flow monitor attached to the first sensor using the first wire member and the second sensor using the second wire member, the blood flow monitor obtaining the first signal and the second signal, removing the anatomical noise data obtained from the second signal from the anatomical noise data obtained by the first signal, and creating an adjusted first signal containing blood flow data from the first signal.

11. The system of claim 10, wherein the blood flow monitor includes a first visual display field, the first visual display field showing the adjusted first signal in graphical form.

12. The system of claim 11, wherein the blood flow monitor includes a second visual display field, the second visual display field showing the second signal in graphical form.

13. The system of claim 10, wherein the retaining member defines an opening that extends from the inner surface to the outer surface; and
    wherein the first wire member is disposed through the opening.

14. The system of claim 13, wherein the second sensor is disposed on the first wire member between the retaining member and the first end of the first wire member.

15. The system of claim 10, wherein the second sensor is disposed on the first wire member a distance from the first sensor between about 5 millimeters and about 15 millimeters.

16. The system of claim 10, wherein the probe has a proximal end, a distal end, and a length extending from the proximal end to the distal end; and
    wherein the second sensor is disposed a distance from the distal end of the probe that is less than 50% of the length of the probe.

17. The system of claim 10, wherein the second sensor is free of attachment to the retaining member.

18. The system of claim 10, wherein the first sensor is a transducer array; and wherein the second sensor is a transducer array.

19. The system of claim 10, wherein the first sensor is releasably attached to the retaining member; and wherein the second sensor is releasably attached to the first wire member.

20. A method of monitoring blood flow through a blood vessel comprising:

placing a tissue flap at a point of treatment, the tissue flap comprising a section of tissue that includes a first blood vessel;

attaching a probe to the tissue flap to monitor blood flow through the first blood vessel, the probe attached to the tissue flap such that a first sensor of the probe contacts the first blood vessel and a second sensor of the probe is free of contact with the first blood vessel, the probe comprising:

a retaining member having a main body defining an outer surface and an inner surface, the retaining member moveable between an open configuration and a closed configuration, the inner surface defining a passageway in the closed configuration;

the first sensor disposed on the inner surface of the retaining member and providing a first signal containing blood flow data and anatomical noise data;

a first wire member attached to the first sensor and having a first end and a second end;

the second sensor disposed on the first wire member between the first end and the second end of the first wire member, the second sensor providing a second signal containing anatomical noise data; and a second wire member attached to the second sensor;

attaching the first sensor to a blood flow monitor using the first wire member, the blood flow monitor having a first visual display field;

attaching the second sensor to the blood flow monitor using the second wire member;

activating the blood flow monitor, the blood flow monitor obtaining the first signal and the second signal, removing the anatomical noise data obtained from the second signal from the anatomical noise data obtained by the first signal, and creating an adjusted first signal containing blood flow data from the first signal, the adjusted first signal shown in graphical form on the first visual display field;

monitoring the adjusted first signal shown in graphical form on the first visual display field over a period of time; and determining if the adjusted first signal shown in graphical form indicates intervention is required, if intervention is required the method further comprises performing treatment to accomplish intervention, if intervention is not required the method further comprises removing the first sensor from the tissue flap.

\* \* \* \* \*